US010842784B2

(12) United States Patent
Nash et al.

(10) Patent No.: US 10,842,784 B2
(45) Date of Patent: Nov. 24, 2020

(54) TREATMENT OF ENERGY UTILIZATION DISEASE

(71) Applicant: Vida Pharma Limited, York (GB)

(72) Inventors: Robert James Nash, Abingdon (GB); Francis Xavier Wilson, Abingdon (GB); Graeme Horne, Abingdon (GB)

(73) Assignee: Vida Pharma Limited, York (GB)

( * ) Notice: Subject to any disclaimer, the term of this patent is extended or adjusted under 35 U.S.C. 154(b) by 364 days.

(21) Appl. No.: 14/974,536

(22) Filed: Dec. 18, 2015

(65) Prior Publication Data
US 2016/0151341 A1 Jun. 2, 2016

Related U.S. Application Data

(63) Continuation of application No. 13/759,173, filed on Feb. 5, 2013, now abandoned, which is a continuation of application No. 12/918,037, filed as application No. PCT/GB2009/000417 on Feb. 17, 2009, now abandoned.

(30) Foreign Application Priority Data

Feb. 18, 2008 (GB) .................................. 0802903.5
Feb. 18, 2008 (GB) .................................. 0802904.3
Feb. 18, 2008 (GB) .................................. 0802907.6

(51) Int. Cl.
*A61K 31/445* (2006.01)
*A61K 36/19* (2006.01)
*A61K 36/815* (2006.01)
*A61K 36/28* (2006.01)
*A61K 31/40* (2006.01)
*A61K 36/27* (2006.01)
*A61K 36/48* (2006.01)
*A61K 36/752* (2006.01)
*A61K 36/42* (2006.01)
*A61K 45/06* (2006.01)

(52) U.S. Cl.
CPC ............ *A61K 31/445* (2013.01); *A61K 31/40* (2013.01); *A61K 36/19* (2013.01); *A61K 36/27* (2013.01); *A61K 36/28* (2013.01); *A61K 36/42* (2013.01); *A61K 36/48* (2013.01); *A61K 36/752* (2013.01); *A61K 36/815* (2013.01); *A61K 45/06* (2013.01)

(58) Field of Classification Search
USPC ........................................................ 514/183
See application file for complete search history.

(56) References Cited

U.S. PATENT DOCUMENTS

| 4,639,436 A | 1/1987 | Junge et al. |
| 5,863,903 A | 1/1999 | Lundgren et al. |
| 2004/0019082 A1 | 1/2004 | Van Der Spoel et al. |

FOREIGN PATENT DOCUMENTS

| EP | 1839661 A2 | 10/2007 |
| WO | 9221657 A1 | 12/1992 |
| WO | 0056334 A1 | 9/2000 |
| WO | 0066105 A2 | 11/2000 |
| WO | 2005092334 A2 | 10/2005 |

OTHER PUBLICATIONS

Shanmugasundaram et. al. (Pharmacological Research Communications (1981) 13: 475-486). (Year: 1981).*
Shanmugasundaram et. al. (Journal of Ethnopharmacology (1990) 30:295-305). (Year: 1990).*
Voss et. al. (Molecular Pharmacology (2007) 71:628-634). (Year: 2007).*
Watson et. al. (Phytochemistry (2001) 56:265-295). (Year: 2001).*
Scheen (Drugs (2003) 63:933-951). (Year: 2003).*
Merrer et. al. (Bioorganic and Medicinal Chemistry (1997) 5:519-533). (Year: 1997).*
Andrew A. Voss et al, Imino Sugars are Potent Agonists of the Human Glucose Sensor SGLT3, Molecular Pharmacology, vol. 71, No. 2, pp. 628-634 (2007).
Gabriela Pistia et al., A General Approach to the Synthesis of Dideoxy and Trideoxyiminoalditols from β-Glycosides, Carbohydrate Research, vol. 328, Issue 4, Oct. 6, 2000 (Abstract only).
Alison A. Watson et al., Polyhydroxylated Alkaloids—Natural Occurrence and Therapeutic Applications, Phytochemistry 56, pp. 265-295 (2001).
Tung M. Fong, Targeting Metabolic Syndrome, Meeting Highlights, Boston, MA May 3-5, 2004.
Cenci Di Bello et al., Specific Inhibition of Human β-D-glucuronidase and α-L-iduronidase by a Trihydroxy Pipecolic Acid of Plant Origin, Federation of European Biochemical Socities, vol. 176, No. 1, pp. 61-64, Oct. 1984.
Yoshimura et al., Synthesis of Both Enantiomers of Hydroxypipecolic Acid Derivatives Equivalent to 5-Azapyranuronic Acids and Evaluation of Their Inhibitory Activities Against Glycosidases, Bioorganic & Medical Chemistry, vol. 16, pp. 8273-8286, (2008).
Scheen (Drugs (2003) 63:933-951).
Merrer et al. (Bioorganic and Medical Chemistry (1997) 5:519-533).
J.G. Cannon, Chapter Nineteen in Burger's Medicinal Chemistry and Drug Discovery, Fifth Edition, vol. I: Principles and Practice, Wiley-Interscience 1995, pp. 783-802.

(Continued)

Primary Examiner — Marcos L Sznaidman
(74) Attorney, Agent, or Firm — Heslin Rothenberg Farley & Mesiti P.C.

(57) ABSTRACT

Described are compositions comprising imino sugar acids for the treatment of energy utilization disease (e.g. metabolic syndrome, including any disease or disorder associated therewith, for example central obesity, elevated levels of triglycerides and diabetes, including type 1 diabetes, type 2 diabetes and insulin resistance), processes for producing said compositions from various plant sources, together with various products, compounds, compositions, medical uses and methods based thereon.

20 Claims, 6 Drawing Sheets

(56) References Cited

OTHER PUBLICATIONS

Kazutaka Miyatake et al., "Isolation of Conduritol a from Gymnema sylvestre and Its Effects against Intestinal Glucose Absorption in Rats" Biosci, Biotech, Biochem, vol. 57, No. 12, pp. 2184-2185. 1993.

E. Porchezhian et al., "An Overview on the Advances of Gymnema Sylvestre: Chemistry, Pharmacology and Patents" Pharmazie, vol. 58, pp. 5-12. 2003.

Parijat Kanetkar et al., "Gymnema Sylvestre: A Memoir" J. Clin. Biochem. Nutr., vol. 41, pp. 77-81. Sep. 2007.

S.J. Persaud et al., "Gymnema Sylvestre Stimulates Insulin Release in vitro by Increased Membrane Permeability" Journal of Endocrinology, vol. 163, pp. 207-212. 1999.

* cited by examiner

TREATMENT OF ENERGY UTILIZATION DISEASE

CROSS REFERENCE TO RELATED APPLICATIONS

This application is a continuation of U.S. patent application Ser. No. 13/759,173, filed Feb. 5, 2013, and published on Jan. 9, 2014 as US2014/0011841. U.S. patent application Ser. No. 13/759,173 is a continuation of U.S. patent application Ser. No. 12/918,037, filed Aug. 17, 2010, and published on Jan. 20, 2011 as US 2011/0015226. U.S. patent application Ser. No. 12/918,037 is a U.S. National Phase filing under 35 U.S.C. § 371 of International Application number PCT/GB2009/000417, filed on Feb. 17, 2009, and published in English on Aug. 27, 2009 as WO 2009/103953. PCT/GB2009/000417 claimed benefit of priority of British application numbers 0802903.5, 0802904.3, and 0802907.6, all of which were filed on Feb. 18, 2008. The entire disclosures of each of these applications are hereby incorporated herein by reference.

FIELD OF THE INVENTION

The present invention relates to compositions for the treatment of energy utilization disease, for example metabolic syndrome (including any disease or disorder associated therewith, for example central obesity, elevated levels of triglycerides and diabetes, including type 1 diabetes, type 2 diabetes and insulin resistance), to processes for producing said compositions from various plant sources, together with various products, compounds, compositions, medical uses and methods based thereon.

The invention also relates to methods for monitoring the quality of a herbal food additive, to processes for producing a herbal food additive as well as to herbal food additives, foods and beverages obtainable by such processes.

BACKGROUND TO THE INVENTION

Imino sugar acids (ISAs) constitute a subclass of the more widely distributed class of phytochemicals known as imino sugars. Many known ISAs are phytochemicals, present as secondary metabolites in plant tissues (where they may play a role in defence).

Structurally, ISAs exhibit great diversity. Many ISAs are small molecules, with molecular weights below 250 Daltons. The skeletons are derived from sugar acids that can be classified structurally on the basis of the configuration of the N-heterocycle: Watson et al. (2001) Phytochemistry 56: 265-295 have classified a comprehensive range of polyhydroxylated alkaloids inter alia as piperidine, pyrroline, pyrrolidine, pyrrolizidine, indolizidine and nortropanes ISAs (see FIGS. 1-7 of Watson et al. (2001), the disclosure of which is incorporated herein by reference).

Although imino sugars are widely distributed in plants (Watson et al., 2001), the imino sugar acids are much less widely distributed. As described herein, the present inventors have discovered that the botanical distribution of imino sugar acids correlates with medicinal plants used for the control of energy utilization disease, including diabetes, obesity and other disorders associated with metabolic syndrome.

Energy Utilization Diseases

Energy utilization diseases encompass a wide range of diseases and include, for example, disorders of homeostasis, metabolic diseases, dysfunction of sugar metabolism and appetite disorders.

Examples of energy utilization diseases therefore include insulin resistance, various forms of diabetes, metabolic syndrome, obesity, wasting syndromes (for example, cancer associated cachexia), myopathies, gastrointestinal disease, growth retardation, hypercholesterolemia, atherosclerosis and age-associated metabolic dysfunction.

Energy utilization diseases also include conditions associated with metabolic syndrome, obesity and/or diabetes, including for example hyperglycaemia, glucose intolerance, hyperinsulinaemia, glucosuria, metabolic acidosis, cataracts, diabetic neuropathy, diabetic nephropathy, diabetic retinopathy, macular degeneration, glomerulosclerosis, diabetic cardiomyopathy, insulin resistance, impaired glucose metabolism, arthritis, hypertension, hyperlipidemia, osteoporosis, osteopenia, bone loss, brittle bone syndromes, acute coronary syndrome, infertility, short bowel syndrome, chronic fatigue, eating disorders and intestinal motility dysfunction.

Insulin Resistance, Metabolic Syndrome and Diabetes

In healthy individuals, blood glucose levels are maintained within a narrow range by two pancreatic hormones: insulin (produced by pancreatic $\beta$-cells) and glucagon (produced by pancreatic $\alpha$-cells). Pancreatic $\beta$-cells sense increases in blood glucose levels and respond by secreting insulin. Insulin promotes glucose uptake by tissues of the body, thereby restoring blood glucose concentration to the physiological range. Glucagon acts reciprocally, increasing blood glucose levels under fasting conditions, primarily by stimulating glucose production in the liver.

Insulin resistance is characterized by a reduced action of insulin in skeletal muscle, adipocytes and hepatocytes so that normal amounts of insulin become inadequate to produce a normal insulin response from the cells of these tissues. In adipocytes, insulin resistance results in hydrolysis of stored triglycerides, leading to elevated free fatty acids in the blood plasma. In muscle, insulin resistance reduces glucose uptake while in hepatocytes it reduces glucose storage. In both of the latter cases an elevation of blood glucose concentrations results.

High plasma levels of insulin and glucose due to insulin resistance often progresses to metabolic syndrome and type 2 diabetes.

Metabolic syndrome is a constellation of abnormalities and disorders that increase the risk of cardiovascular disease and diabetes. The incidence is very high in many developed countries: some studies indicate prevalence in the USA of up to 25% of the population. The disorder is also known as (metabolic) syndrome X, insulin resistance syndrome, Reaven's syndrome and CHAOS. Metabolic syndrome may be diagnosed by the presence of three or more of the following symptoms: central obesity (waist measurement of more than 40 inches for men and more than 35 inches for women); high levels of triglycerides (150 mg/dL or higher); low levels of HDL (below 40 mg/dL for men and below 50 mg/dL for women) and high blood pressure (130/85 mm Hg or higher). Associated diseases and signs are: fatty liver (often progressing to non-alcoholic fatty liver disease), polycystic ovarian syndrome, hemochromatosis (iron overload) and acanthosis nigricans (dark skin patches).

The first line treatment of metabolic syndrome is change of lifestyle (caloric restriction and physical activity). However, drug treatment is frequently required. Generally, the individual diseases that comprise the metabolic syndrome are treated separately (e.g. diuretics and ACE inhibitors for hypertension). Cholesterol drugs may be used to lower LDL cholesterol and triglyceride levels, if they are elevated, and to raise HDL levels if they are low. Use of drugs that decrease insulin resistance (e.g. metformin and thiazolidinediones is controversial). A recent study indicated that cardiovascular exercise was therapeutic in less than 31% of cases, the most probable benefit was to triglyceride levels, with 43% showing improvement; conversely 91% of test subjects did not exhibit a decrease in fasting plasma glucose or insulin resistance.

Type 2 diabetes is a chronic disease that is characterised by persistently elevated blood glucose levels (hyperglycaemia). Insulin resistance together with impaired insulin secretion from the pancreatic β-cells characterizes the disease. The progression of insulin resistance to type 2 diabetes is marked by the development of hyperglycaemia after eating when pancreatic β-cells become unable to produce adequate insulin to maintain normal blood sugar levels (euglycemia)).

The most important drug currently used to treat type 2 diabetes is metformin (Glucophage, Diabex, Diaformin, Fortamet, Riomet, Glumetza, Cidophage and others). Metformin is of the biguanide class of oral antihyperglycaemic agents. Other biguanides include phenformin and buformin (now withdrawn). Metformin works primarily by reducing liver release of blood glucose from glycogen stores, but also has some effect in increasing the uptake of glucose. Other widely used drug classes include those of the sulfonylurea group (including glibenclamide and gliclazide). These drugs increase glucose stimulated insulin secretion by the pancreas. Newer drug classes include thiazolidinediones (e.g. rosiglitazone, pioglitazone, and troglitazone), which act by binding to PPARs (peroxisome proliferator-activated receptors), a group of receptor molecules inside the cell nucleus. Other classes include α-glucosidase inhibitors (acarbose and miglitol), meglitinides (which stimulate insulin release and include nateglinide, repaglinide and their analogues), peptide analogs (e.g. incretin mimetics, which act as insulin secretagogues, glucagon-like peptide analogues (e.g. exenatide), dipeptidyl peptidase-4 (DPP-4) inhibitors (which increase incretin levels (e.g. sitagliptin) and amylin agonist analogues (which slow gastric emptying and suppress glucagon (e.g. pramlintide).

However, no existing therapies for the different forms of type 2 diabetes seem to improve function of key intrinsic factors in the β-cells and all existing therapies fail to arrest progression of the disease and, over time, also fail to normalise glucose levels and/or prevent subsequent complications. The existing therapies are also associated with undesirable side effects. For example, insulin secretagogues and insulin injections may cause hypoglycaemia and weight gain. Patients may also become unresponsive to insulin secretagogues over time. Metformin and α-glucosidase inhibitors often lead to gastrointestinal problems and PPAR agonists tend to cause increased weight gain and oedema. Exenatide is also reported to cause nausea and vomiting.

Type 1 diabetes (or insulin dependent diabetes) is characterized by loss of the insulin-producing beta cells of the islets of Langerhans in the pancreas, leading to a deficiency of insulin. The main cause of this beta cell loss is a T-cell mediated autoimmune attack. There is no known preventative measure that can be taken against type 1 diabetes, which comprises up to 10% of diabetes mellitus cases in North America and Europe. Most affected people are otherwise healthy and of a healthy weight when onset occurs. Sensitivity and responsiveness to insulin are usually normal, especially in the early stages.

The principal treatment of type 1 diabetes, even from the earliest stages, is replacement of insulin combined with careful monitoring of blood glucose levels using blood-testing monitors. Without insulin, ketosis and diabetic ketoacidosis can develop and coma or death will result. Apart from the common subcutaneous injections, it is also possible to deliver insulin by a pump, which allows continuous infusion of insulin 24 hours a day at preset levels, and the ability to program doses (a bolus) of insulin as needed at meal times. An inhaled form of insulin, Exubera, has recently been approved by the FDA.

The treatment of type 1 diabetes must be continued indefinitely. While treatment does not impair normal activities, great awareness, appropriate care, and discipline in testing and medication must be observed.

Thus, new and/or alternative antidiabetic drug treatments, particularly those that are able to restore β-cell function, are required. In particular, there is a real and substantial unmet clinical need for an effective drug that is capable of treating both type 2 and type 1 diabetes and associated conditions with fewer side effects than existing drug therapies as well as treatments for metabolic syndrome are required, particularly treatments which are effective against obesity and/or elevated triglyceride levels.

Herbal Food Additives and Remedies

There is presently great interest in the use of herbal remedies and supplements and a growing acceptance from food manufacturers, healthcare companies and the medical profession that herbal products have value and can complement established formulations and treatments. Herbal food additives and supplements are now widely used. In particular, demand for low-carbohydrate, low-sugar food alternatives has led to a growing interest in natural sweeteners and steviol glycosides (responsible for the sweet taste of the leaves of the *stevia* plant (*Stevia rebaudiana*)) are being developed by Coca Cola as natural sweeteners.

However, quality control of herbal food additives is difficult due to the complex nature and inherent non-uniformity of plant materials. The materials used in herbal and plant-based food additive are usually whole plants or parts or extracts thereof. Since plant materials contain many different chemical components the materials are complex mixtures. This makes it very difficult to standardize and control the quality of the materials. Moreover, many herbal food additives are mixtures of two or more plant-based components and are therefore mixtures of mixtures, so introducing a further level of complexity. Furthermore, the recipes and methods of manufacture used are often not uniform and may remain undisclosed. These factors make it very difficult to ensure that two samples of a given product, obtained from disparate sources and ostensibly identical, do in fact contain the same mixture of ingredients. This problem, which leads to difficulties in controlling the quality of such materials, has limited the use of certain herbal extracts even amongst herbal practitioners.

Such problems may be particularly acute in the case of *Stevia*-derived products, since certain steviosides have been reported to have possible mutagenic activity and hence fractionating *Stevia*-derived plant material to remove such material may be of particular importance. Other problems arise from the fact that the plants used in the practice of herbal food additive are frequently unavailable locally and therefore need to be obtained from sources which are remote from the end user. However, the supply of such plants from remote locations can be erratic and inaccurate, particularly because no detailed monographs including identity and quality standards exist for many such plants. The complex mixture of ingredients found in medicinal plants varies widely in type and concentration depending on many factors including the botanical source, the location where the plant is grown, what other plants or microorganisms are growing near it, the time of year when the plant is harvested, the conditions under which the material is stored and processed and the extraction procedure used.

There is therefore a need for sensitive processes which can profile herbal products and so establish a standard specification for a medicinal plant material which can be related to activity, so permitting quality control in the production of herbal food additives and ideally quantifying the components known or likely to be active.

The imino sugar acids are analogues of sugar acids in which the ring oxygen is replaced by a nitrogen. Although imino sugars are widely distributed in plants (Watson et al. (2001) Phytochemistry 56: 265-295), the imino sugar acids are much less widely distributed. The present inventors have now discovered that the botanical distribution of imino sugar acids correlates with medicinal plants used for the control of diabetes and obesity. Imino sugar acids have not hitherto been reported from these plants, possibly because carbohydrate-like compounds are difficult to analyse using the conventional HPLC analytical systems and compounds affecting sugar perception in these plants have attracted more interest. Thus, qualitative and/or quantitative analysis of herbal material for imino sugar acids can form the basis of quality control procedures during the sourcing, preparation and processing of herbal food additives and foods/beverages based thereon, particularly those foods and beverages formulated to form part of a low-calorie or low-sugar diet. In some applications it may be important to ensure that imino sugar acids are absent from the herbal material in order to ensure that inappropriate or undesirable pharmaceutical activities are eliminated from the supplemented foodstuff or beverage.

SUMMARY OF THE INVENTION

The present invention is based, at least in part, on the surprising discovery that the botanical distribution of imino sugar acids correlates with medicinal plants used for the control of diabetes, obesity and other disorders associated with metabolic syndrome. Thus, for the first time ISAs have been identified as important bioactive principles in established anti-obesity and anti-diabetic herbal medicines.

Thus, according to the invention there is provided an isolated imino sugar acid for the treatment of an energy utilization disease (for example metabolic syndrome, including type 1, type 2 diabetes and insulin resistance) as well as a nutraceutical or pharmaceutical composition comprising an isolated imino sugar acid.

Thus, according to the invention there is provided a process for the production of a composition for the treatment of energy utilization disease (for example metabolic syndrome (including type 1, type 2 diabetes and insulin resistance) comprising the steps of:
(a) providing plant material;
(b) isolating one or more imino sugar acid(s) from said plant material (and optionally removing or reducing potential toxins); and then
(c) formulating said isolated imino sugar acid(s) with a pharmaceutical excipient to produce an anti-metabolic syndrome composition in which the amount and concentration of the isolated imino sugar acid(s) is sufficient to treat the energy utilization disease in a human subject.

The invention contemplates synthetic analogues of the naturally-occurring ISAs described herein. Such synthetic analogues may be produced by a process comprising the steps of: (a) isolating one or more imino sugar acid(s) from plant material; (b) determining the structure of said ISA; and then (c) synthesising said synthetic ISA analogue. Thus, the invention contemplates a process for the production of an ISA for the treatment of metabolic syndrome and/or diabetes (including type 1 and type 2 diabetes and insulin resistance) comprising the steps of: (a) isolating one or more imino sugar acid(s) from plant material; (b) determining the structure of said ISA; and then (c) synthesising said ISA to produce a synthetic ISA for use in the treatment of metabolic syndrome and/or diabetes (including type 1 and type 2 diabetes and insulin resistance).

The invention contemplates synthetic derivatives of the naturally occurring ISAs described herein. Such synthetic derivatives may be produced by a process comprising the steps of: (a) isolating one or more imino sugar acid(s) from plant material; and then (b) derivatizing said isolated ISA (e.g. chemically or enzymatically) to produce a synthetic ISA derivative. Thus, the invention contemplates a process for the production of an ISA for the treatment of metabolic syndrome and/or diabetes (including type 1 and type 2 diabetes and insulin resistance) comprising the steps of: (a) isolating one or more imino sugar acid(s) from plant material; and then (b) derivatizing said isolated ISA (e.g. chemically or enzymatically) to produce a synthetic ISA derivative.

The plant material used as starting material in step (a) is preferably derived from a botanical source selected from: (a) *Stevia* spp. (e.g. *S. rebaudiana*); (b) *Gymnema* spp. (e.g. *G. sylvestre*); (c) *Andrographis* spp. (e.g. *A. paniculata*); (d) leguminous species (e.g. *Aspalanthus linearis* (Rooibos), *Baphia* spp., *Glycine max* (soya), *Alexa* spp.), *Castanospermum australe*), *Lotus* spp.; (e) plants of the family Rutaceae (for example *Citrus* spp., e.g. *C. aurantium*), (f) plants of the Cucurbitaceae (for example Asian Pumpkin, *Cucurbita ficifolia* and *Momordica charantia*) or (g) Solanaceae (e.g. *Lycium barbarum*, Goji).

The imino sugar acid is preferably of a structural class selected from piperidine, pyrrolidine, pyrroline, pyrrolizidine, indolizidine and nortropane ISAs.

In another aspect, the invention contemplates an anti-metabolic syndrome and/or anti-diabetes (including type 1 and type 2 diabetes and insulin resistance) composition obtainable by the process of any one of the preceding claims for use as an anti-metabolic syndrome and/or anti-diabetes (including type 1 and type 2 diabetes and insulin resistance) agent.

In another aspect, the invention contemplates an anti-metabolic syndrome and/or anti-diabetes (including type 1 and type 2 diabetes and insulin resistance) composition obtained by the process of the invention.

In another aspect, the invention contemplates a process for producing a pharmaceutical composition comprising the step of monitoring the quality of said composition by detecting the presence or absence or measuring the amount of an imino sugar acid in a sample of said composition. Such embodiments find particular application in processes for the production of anti-diabetic drugs based on purification from natural plant sources.

In another aspect, the invention contemplates a method for monitoring the quality of a pharmaceutical composition comprising the steps of: (a) providing a sample of the composition; and (b) detecting the presence or absence or measuring the amount of an imino sugar acid in said sample. Again such embodiments find particular application in processes for the production of anti-diabetic drugs based on purification from natural plant sources.

The latter two embodiments find particular application in the production of anti-diabetic drugs based on isolation from

*Gymnema* spp. (e.g. from *G. sylvestre*, *Aspalanthus*, *Glycine max*, *Lycium*, *Momordica* or *Cucurbita* species).

Certain ISAs described herein are novel. According to the invention, we also provide those novel ISAs as products per se, together with processes for their preparation, compositions containing them, as well as their use as pharmaceuticals. Some of the ISAs described herein are known, as such, but not as pharmaceuticals. According to the invention, we claim as pharmaceuticals per se such ISAs as are known in the art but which are not previously described for use as pharmaceuticals.

Herbal Quality Monitoring Aspects of the Invention

According to another aspect of the present invention there is provided a process for producing a herbal food additive comprising the step of monitoring the quality of said herbal food additive by detecting the presence or absence or measuring the amount of an imino sugar acid in a sample of said herbal food additive.

In another aspect, the invention provides a method for monitoring the quality of a herbal food additive comprising the steps of: (a) providing a sample of the herbal food additive; and (b) detecting the presence or absence or measuring the amount of an imino sugar acid in said sample.

In this context, the term quality is used to define the overall fitness of the herbal food additive for its intended use, and may include for example the presence or absence of one or more phytochemicals (at an appropriate concentration) which indicates the use of a particular source, condition, purity and an acceptable or unacceptable degree of contamination with undesirable supplements and/or contaminants.

In circumstances where a desirable biological activity is associated with the imino sugar acid (e.g. anti-obesity or anti-diabetic activity), the invention preferably comprises the step of monitoring the quality of said herbal food additive by detecting the presence or measuring the amount of an imino sugar acid in a sample of said herbal food additive.

However, in circumstances where a biological activity is associated with the imino sugar acid (e.g. glycosidase inhibitory activity, anti-obesity or anti-diabetic activity) but it is desired to eliminate such activity from the food additive, the process of the invention preferably comprises the step of monitoring the quality of said herbal food additive by detecting the absence of an imino sugar acid in a sample of said herbal food additive. Such embodiments of the invention may find particular application in circumstances where: (a) the herbal food additive is derived from a plant source which is known to contain imino sugar acids together with other phytochemicals and (b) where the other phytochemicals but not the imino sugar acids are required. Such circumstances may arise, for example, in cases where the herbal food additive comprises *Stevia*-derived material containing both imino sugar acids and steviol glycosides and where a food additive comprising steviol glycosides free of imino sugar acids is required (e.g. to serve as a natural sweetener with no additional biological activity).

In the latter embodiments, the step of monitoring the quality of said herbal food additive by detecting the absence of an imino sugar acid in a sample of said herbal food additive typically takes the form of an analytical step which yields an upper limit value for the concentration of the imino sugar acid analyte and need not be such as to confirm absolute absence of imino sugar acid. In many cases, the step is such as to yield a value which can be used to confirm that the concentration of imino sugar acid(s) in the sample falls below a particular threshold value. In such circumstances the threshold value will depend on the use to which the herbal food additive is to be put. In most cases it will reflect a concentration below which the biological effects of the imino sugar acids are acceptable (e.g. undetectable) when the herbal additive is in use.

In a further aspect, the invention provides a process for producing a supplemented foodstuff or beverage comprising the steps of:
(a) providing a herbal food additive;
(b) monitoring the quality of said herbal food additive of step (a) according to the method of the invention; and
(c) adding the herbal food additive to a foodstuff or beverage to produce said supplemented foodstuff or beverage.

This aspect of the invention finds broad utility in the production of any supplemented foodstuff or beverage and any foodstuff or beverage may be used, including chilled foods and beverages, hot foods and beverages, sweetened foods and beverages, carbonated beverages, alcoholic beverages and non-alcoholic beverages. The supplemented foodstuff or beverage is preferably a carbonated beverage.

Particularly preferred are beverages or foodstuffs which are sweetened with one or more steviol glycosides. In such embodiments, the steviol glycosides are preferably selected from: (a) stevioside; (b) rebaudioside; and (c) dulcoside A. For example, the steviol glycoside preferably comprise or consist essentially of isolated rebaudioside A, B, C, D and/or E. Particularly preferred are beverages or foodstuffs consisting essentially of rebaudioside A.

Any herbal food additive may be used according to the invention, but preferred are herbal food additives derived from *Stevia* spp., *Gymnema* spp. (for example *Gymnema sylvestre*), *Citrus* spp., *Aspalanthus linearis* (Rooibos), *Glycine max* (Soya), Pumpkin (*Cucurbita ficifolia* and other Cucubitaceae species, e.g. *Momordica charantia*), *Lycium barbarum* (Goji) or mixtures thereof.

The processes and methods of the invention preferably further comprise the step of detecting the presence or absence or measuring the amount of an imino sugar in said sample of herbal food additive. In such embodiments, the imino sugar and/or imino sugar acid may be of a structural class selected from piperidine, pyrrolidine, pyrrolizidine, indolizidine and nortropane. In preferred embodiments, the imino sugar is a glycosidase inhibitor (e.g. a glucosidase or glucuronidase inhibitor).

In embodiments where the presence or absence of imino sugars or imino sugar acids are detected according to the invention, preferred are processes in which the presence or absence of pyrrolidine imino sugars or imino sugar acids is detected. Particularly preferred is 2,5-dihydroxymethyl-3,4-dihydroxypyrrolidine (DMDP) or derivatives thereof. The latter embodiment is particularly preferred in cases where the herbal food additive comprises *Stevia*-derived material containing both DMDP and derivatives and steviol glycosides and where a food additive comprising steviol glycosides free of DMDP or derivatives is required (e.g. to serve as a natural sweetener with no additional biological activity).

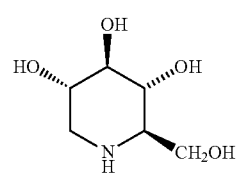

-continued

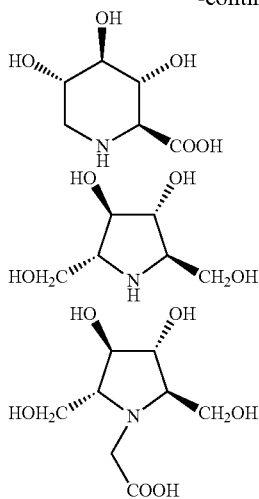

Examples of imino sugars (deoxynojirimycin, DNJ at top left; DMDP at bottom left) and imino sugar acids derived from them The imino sugar acid used as analyte in the processes and methods of the invention may be any imino sugar acid, including piperidine, pyrroline, pyrrolidine, pyrrolizidine, indolizidine and nortropane imino sugar acids. Preferred are piperidine imino sugar acids (e.g. pipecolic acids).

The imino sugar and/or imino sugar acid used as analyte in the processes and methods of the invention is preferably polyhydroxylated.

The herbal food additive is preferably plant material or one or more phytochemicals derived from *Stevia* spp., for example *Stevia rebaudiana*.

The invention also contemplates a herbal food additive obtainable by the methods and processes of the invention.

BRIEF DESCRIPTION OF THE DRAWINGS

FIG. 5A is given by oral route, FIG. 5B is given by oral administration 30 minutes before intraperitoneal injection, and FIG. 5C is given by oral administration 30 minutes before maltose-loading.

DETAILED DESCRIPTION OF THE INVENTION

Definitions and General Preferences

Figure 1A:
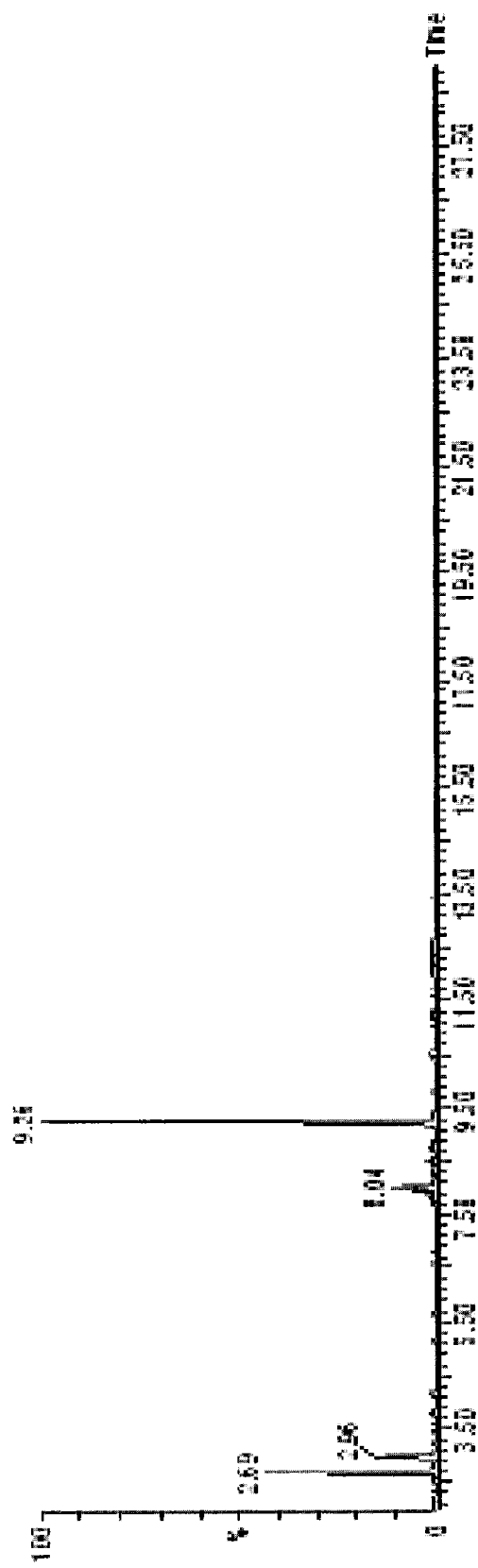
FIG. 1 shows the GC-MS chromatogram of *Gymnema* water extract (FIG. 1(a)), the characteristic mass spectrum (tms) of imino sugar acid G2 (FIG. 1(b)), and the GC-MS chromatogram of water extract of *Stevia rebaudiana* (FIG. 1(c)).

Where used herein and unless specifically indicated otherwise, the following terms are intended to have the following meanings in addition to any broader (or narrower) meanings the terms might enjoy in the art:

As used herein, the term "energy utilization disease" encompasses any disease or disorder arising from abnormal energy utilization. The term therefore covers disorders and diseases of homeostasis, metabolic disease, dysfunction of sugar metabolism and appetite disorders. The term therefore includes insulin resistance, various forms of diabetes, metabolic syndrome, obesity, wasting syndromes (for example, cancer associated cachexia), myopathies, gastrointestinal disease, growth retardation, hypercholesterolemia, atherosclerosis and age-associated metabolic dysfunction. The term also covers conditions associated with metabolic syndrome, obesity and/or diabetes, including for example hyperglycaemia, glucose intolerance, hyperinsulinaemia, glucosuria, metabolic acidosis, cataracts, diabetic neuropathy, diabetic nephropathy, diabetic retinopathy, macular degeneration, glomerulosclerosis, diabetic cardiomyopathy, insulin resistance, impaired glucose metabolism, arthritis, hypertension, hyperlipidemia, osteoporosis, osteopenia, bone loss, brittle bone syndromes, acute coronary syndrome, infertility, short bowel syndrome, chronic fatigue, eating disorders and intestinal motility dysfunction.

References herein to the treatment of metabolic syndrome are to be interpreted to include the treatment of any or all of the disorders associated with metabolic syndrome, including in particular obesity (e.g. central obesity), and elevated serum triglycerides and diabetes (including type 1 and type 2 diabetes and insulin resistance).

The term imino sugar acid defines a sugar acid analogue in which the ring oxygen is replaced by a nitrogen. The term N-acid ISA defines an imino sugar acid in which the carboxylic acid group is located on the ring nitrogen. The term N-acid derivative defines imino sugar analogues in which the ring nitrogen is substituted with a carboxylic acid group.

Preferred ISAs are selected from the following structural classes: piperidine (including (poly)hydroxypipecolic acids); pyrroline; pyrrolidine (including (poly)hydroxyprolines); pyrrolizidine; indolizidine and nortropane.

As used herein, the term polyhydroxylated as applied to imino sugar acids defines an ISA having at least 2 (preferably at least 3) free hydroxyl (or hydroxyalkyl) groups on the ring system nucleus.

The term isolated as applied to the ISAs of the invention is used herein to indicate that the ISA exists in a physical milieu distinct from that in which it occurs in nature (or in the case of synthetic, non-naturally-occurring ISAs, is purified). For example, the isolated material may be substantially isolated (for example purified) with respect to the complex cellular milieu in which it naturally occurs.

When the isolated material (e.g. synthetic, non-naturally occurring ISA) is purified, the absolute level of purity is not critical and those skilled in the art can readily determine appropriate levels of purity according to the use to which the material is to be put. Preferred, however, are purity levels of 90% w/w, 99% w/w or higher. In some circumstances, the isolated ISA forms part of a composition (for example a more or less crude extract containing many other substances) or buffer system, which may for example contain other components. In other circumstances, the isolated ISA may be purified to essential homogeneity, for example as determined spectrophotometrically, by NMR or by chromatography (for example GC-MS of the trimethylsilyl-derivatives).

The term phytochemical is used herein in a broad sense to encompass any chemical constituent of a plant, including macromolecules and small molecules. Important examples include alkaloids (for example imino sugars and imino sugars acids, e.g. selected from the structural classes pyrrolidines, piperidines, pyrrolizidines, indolizidines, tropanes and nortropanes), carbohydrate analogues, phenolic compounds, terpenoids, enzyme inhibitors, glycosides, nucleotides, amino acids, lipids and sugars.

The terms derivative and pharmaceutically acceptable derivative as applied to the ISAs of the invention define ISAs which are obtained (or obtainable) by chemical derivatization of the parent ISAs of the invention. The pharmaceutically acceptable derivatives are suitable for administration to or use in contact with the tissues of humans without undue toxicity, irritation or allergic response (i.e. commensurate with a reasonable benefit/risk ratio). Preferred derivatives are those obtained (or obtainable) by alkylation, esterification or acylation of the parent ISAs of the invention. Particularly preferred are acyl (e.g. butyl) derivatives, for example O-acyl (e.g. O-butyl) derivatives. N-acid imino sugar acids are also preferred.

The derivatives may be antidiabetic per se, or may be inactive until processed in vivo. In the latter case, the derivatives of the invention act as pro-drugs. Particularly preferred pro-drugs are ester derivatives which are esterified at one or more of the free hydroxyls and which are activated by hydrolysis in vivo. The pharmaceutically acceptable derivatives of the invention retain some or all of the antidiabetic activity of the parent ISA. In some cases, the activity is increased by derivatization. Derivatization may also augment other biological activities of the ISA, for example bioavailability and/or glycosidase inhibitory activity and/or glycosidase inhibitory profile. For example, derivatization may decrease glycosidase inhibitory potency and/or increase specificity.

Imino sugar acids of the invention which do not inhibit glucosidase activity (or do not inhibit glucosidase activity to a clinically-significant extent) may exhibit no detectable inhibitory activity or may be poor inhibitors, for example exhibiting $IC_{50}$ values in the μM or mM ranges or greater. Typically, clinically significant glucosidase inhibition arises only when compounds have $IC_{50}$ values in the submicromolar range. In such embodiments, the glucosidase may be a mammalian α-glucosidase, for example an α-glucosidase and/or a digestive α-glucosidase (for example, a disaccharidase such as saccharase), so that the imino sugar acid may exhibit no detectable inhibitory activity (or may exhibit $IC_{50}$ values in the μM or mM ranges or greater) in respect of these enzyme classes.

Imino sugar acids of the invention which do not inhibit glucosidase activity (or do not inhibit glucosidase activity to a clinically-significant extent) may spare the activity of desirable glucosidase activity in vivo, and in particular may spare digestive glucosidase activity to the extent that adverse gastric side-effects seen with the use of known anti-diabetic imino sugar agents (such as miglitol) are reduced or eliminated.

The term pharmaceutically acceptable salt as applied to the ISAs of the invention defines any non-toxic organic or inorganic acid addition salt of the free base compounds which are suitable for use in contact with the tissues of humans and lower animals without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid). The ISA drugs of the invention may also be converted into salts by reaction with an alkali metal halide, for example sodium chloride, sodium iodide or lithium iodide. Preferably, the ISAs of the invention are converted into their salts by reaction with a stoichiometric amount of sodium chloride in the presence of a solvent such as acetone.

These salts and the free base compounds can exist in either a hydrated or a substantially anhydrous form. Crystalline forms of the compounds of the invention are also contemplated and in general the acid addition salts of the ISAs of the invention are crystalline materials which are soluble in water and various hydrophilic organic solvents and which in comparison to their free base forms, demonstrate higher melting points and an increased solubility.

The term herbal medicine is used herein to define a pharmaceutical composition in which at least one active principle is not chemically synthesized and is a phytochemical constituent of a plant. In most cases, this non-synthetic active principle is not isolated (as defined herein), but present together with other phytochemicals with which it is associated in the source plant. In some cases, however, the plant-derived bioactive principle(s) may be in a concentrated fraction or isolated (sometimes involving high degrees of purification). In many cases, however, the herbal medicine comprises a more or less crude extract, infusion or fraction of a plant or even an unprocessed whole plant (or part thereof), though in such cases the plant (or plant part) is usually at least dried and/or milled.

The term herbal food additive is used herein to define a composition in which at least one component is not chemically synthesized but rather is a phytochemical constituent of a plant. In most cases, this non-synthetic component is not purified, but present together with other phytochemicals with which it is associated in the source plant. In some cases, however, the plant-derived component(s) may be in a concentrated fraction or isolated (sometimes to high degrees of purity). In many cases, however, the herbal food additive comprises a more or less crude extract, infusion or fraction of a plant or even an unprocessed whole plant (or part thereof), though in such cases the plant (or plant part) is usually at least dried and/or milled.

The term bioactive principle is used herein to define a phytochemical which is necessary or sufficient for the pharmaceutical efficacy of the herbal medicament in which it is comprised. In the case of the present invention, the bioactive principle comprises the antidiabetic ISA of the invention (e.g. a compound of formula (G2)).

The term standard specification is used herein to define a characteristic, or a phytochemical profile, which is correlated with an acceptable quality of the herbal medicine. In this context, the term quality is used to define the overall fitness of the herbal medicament for its intended use, and includes the presence of one or more of the bioactive principles (at an appropriate concentration) described above or else the presence of one or more bioactive markers or a phytochemical profile which correlates with the presence of one or more of the bioactive principles (at an appropriate concentration).

The term phytochemical profile is used herein to define a set of characteristics relating to different phytochemical constituents.

In its broadest aspect, the present invention contemplates all optical isomers, racemic forms and diastereomers of the ISAs of the invention. Those skilled in the art will appreciate that, owing to the asymmetrically substituted carbon atoms present in the ISAs of the invention, the ISAs of the invention may exist and be synthesised and/or isolated in optically active and racemic forms. Thus, references to the ISAs of the present invention encompass the ISAs as a mixture of diastereomers, as individual diastereomers, as a mixture of enantiomers as well as in the form of individual enantiomers.

Therefore, the present invention contemplates all optical isomers and racemic forms thereof of the ISAs of the invention, and unless indicated otherwise (e.g. by use of dash-wedge structural formulae) the compounds shown herein are intended to encompass all possible optical isomers of the compounds so depicted. In cases where the stereochemical form of the ISA is important for pharmaceutical utility, the invention contemplates use of an isolated eutomer. Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation.

Imino Sugar Acids of the Invention

The imino sugar acids (ISAs) are analogues of sugar acids in which the ring oxygen is replaced by a nitrogen. Although imino sugars are widely distributed in plants (Watson et al. (2001) Phytochemistry 56: 265-295), the imino sugar acids are much less widely distributed.

Imino sugar acids can be classified structurally on the basis of the configuration of the N-heterocycle. Examples include piperidine, pyrroline, pyrrolidine, pyrrolizidine, indolizidine and nortropanes imino sugar acids (see FIGS. 1-7 of Watson et al. (2001), the disclosure of which is incorporated herein by reference).

Particularly preferred are imino sugar acids selected from the following structural classes:
(a) piperidine ISAs (including (poly)hydroxypipecolic acids);
(b) pyrroline ISAs;
(c) pyrrolidine ISAs (including (poly)hydroxyprolines);
(d) pyrrolizidine ISAs;
(e) indolizidine ISAs; and
(f) nortropane ISAs.

However, ISA mixtures or combinations containing two or more different ISAs representative of one or more of the classes listed above may also be used.

Preferred are polyhydroxylated ISAs. Particularly preferred are ISAs having a small molecular weight, since these may exhibit desirable pharmacokinetics. Thus, the ISA may have a molecular weight of 100 to 400 Daltons, preferably 150 to 300 Daltons and most preferably 200 to 250 Daltons.

Also preferred are ISAs, which are analogues of hydroxymethyl-substituted imino sugars in which one or more hydroxymethyl groups are replaced with carboxyl groups.

Exemplary Piperidine Imino Sugar Acids

The ISA of the invention may be a piperidine ISA having at least 3 free hydroxyl (or hydroxyalkyl) groups on the ring system nucleus. Exemplary piperidine ISAs are hydroxypipecolic acids. Particularly preferred hydroxypipecolic acids are polyhydroxypipecolic acids having at least two (e.g. 3) free hydroxyl (or hydroxyalkyl) groups on the ring system nucleus. Also contemplated are N-acid derivatives of the foregoing and N-acid derivatives of piperidine imino sugars such as 1-deoxynojirimycin.

Exemplary piperidine ISAs according to the invention are compounds of formula (I):

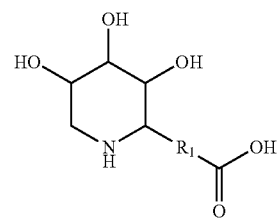

wherein
$R_1$ is absent or is $C_1$-$C_6$ alkyl;
the location of the carboxyl group may be switched from the ring carbon to the ring nitrogen to produce an N-acid analogue of the compound of formula (I);
or an acyl (e.g. O-acyl) derivative or dehydroxylated analogue in which one or more ring hydroxyl(s) are absent;
or a pharmaceutically acceptable salt or derivative thereof.

Thus, exemplary piperidine ISAs according to the invention may be selected from the structures shown below:

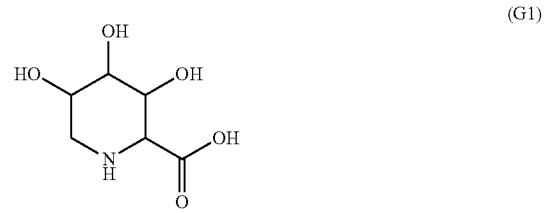

(G1)

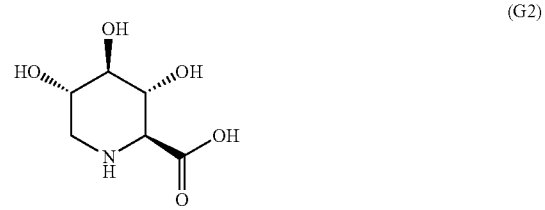

(G2)

(G3)

(G4)

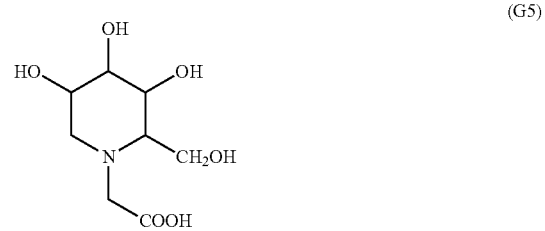

(G5)

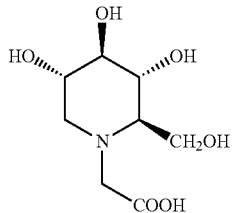

(G6)

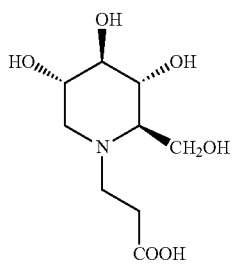

T1

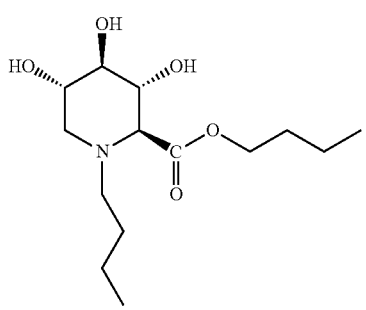

T2

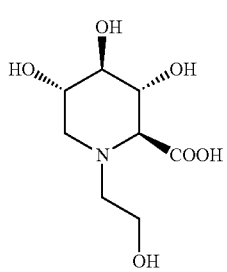

T3

Also specifically contemplated are: (a) N-acid analogues of the foregoing structures (G1)-(G4) in which the location of the carboxyl group is switched from the ring carbon to the ring nitrogen; (b) acyl (e.g. O-acyl) derivatives of the foregoing structures (or of the N-acid analogues of (a)); (c) dehydroxylated analogues of the foregoing structures (or of the N-acid analogues of (a) and (b)) in which one or more ring hydroxyl(s) are absent.

The compound of formula (G2) was first isolated from the legume *Baphia racemosa* (Fabaceae) (see Booth et al., 2007: (2R,3R,4R,5S)-3,4,5-*trihydroxypipecolic acid dihydrate* [(2S,3R,4R,5S-*trihydroxypiperidine*-2-*carboxylic acid dihydrate* Acta Crystalographica Section E63, 3783-3784 and references therein) but the present inventors have now discovered that it is a major component of *Gymnema sylvestre* (Asclepiadaceae). Although *G. sylvestre* is widely claimed to have anti-diabetic and weight control activity, most attention has focused on gymnemic acids which can temporarily block sugar taste. These gymnemic acids and other glycosides (saponins) appear to have some of the anti-diabetic activity of the plant when tested in animal models. The activity of these compounds appears to be due to affects on membrane permeability in vitro although due to similar chemical properties, imino sugar acids may well unknowingly also have been present; it is not clear in our opinion that this effect on membrane permeability would affect the pancreas in vivo (Persaud et al., 1999, J. Endocrinol.: 163:207-12).

Piperidine ISAs for use according to the invention may be isolated for example from *Gymnema* spp. (e.g. *G. sylvestre*) (see Example 1, below).

Exemplary Pyrrolidine Imino Sugar Acids

The ISA of the invention may be pyrrolidine ISAs having at least 1 (preferably at least 2 or 3) free hydroxyl (or hydroxyalkyl) groups on the ring system nucleus. Preferred pyrrolidine ISAs are hydroxyprolines. Particularly preferred hydroxyprolines are polyhydroxyprolines having at least two (e.g. at least 3) free hydroxyl (or hydroxyalkyl) groups on the ring system nucleus. Also contemplated are N-acid derivatives of the foregoing.

Exemplary pyrrolidine ISAs according to the invention may be selected from the structures shown below:

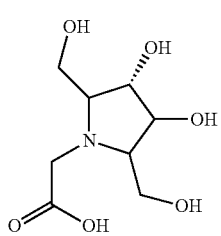

(S1)

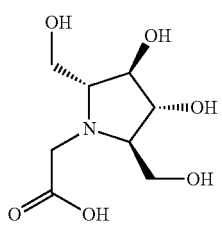

(S2)

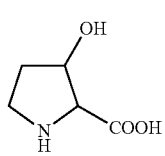

(S3)

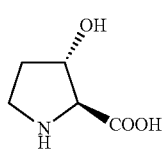

(S4)

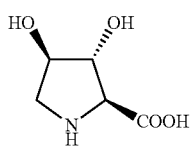

(S3')

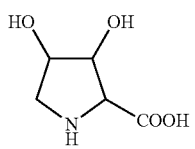

(S4')

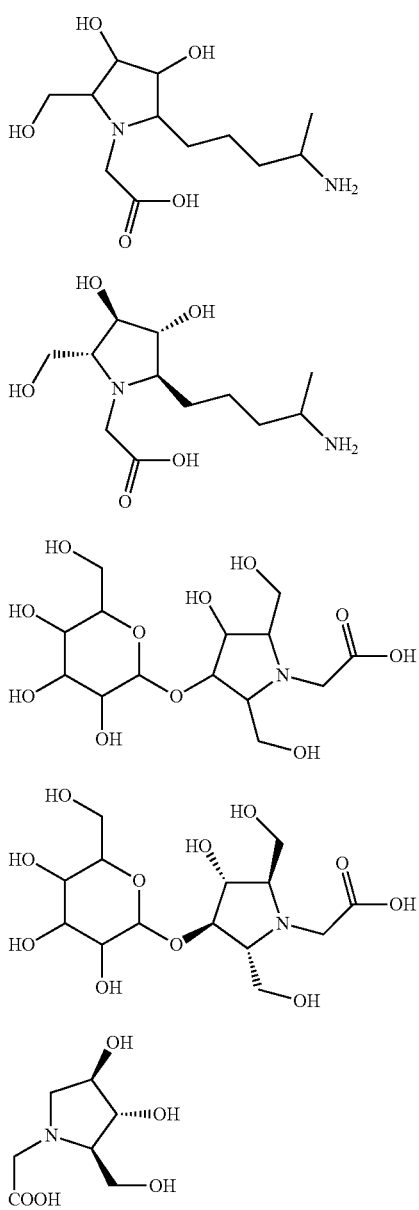

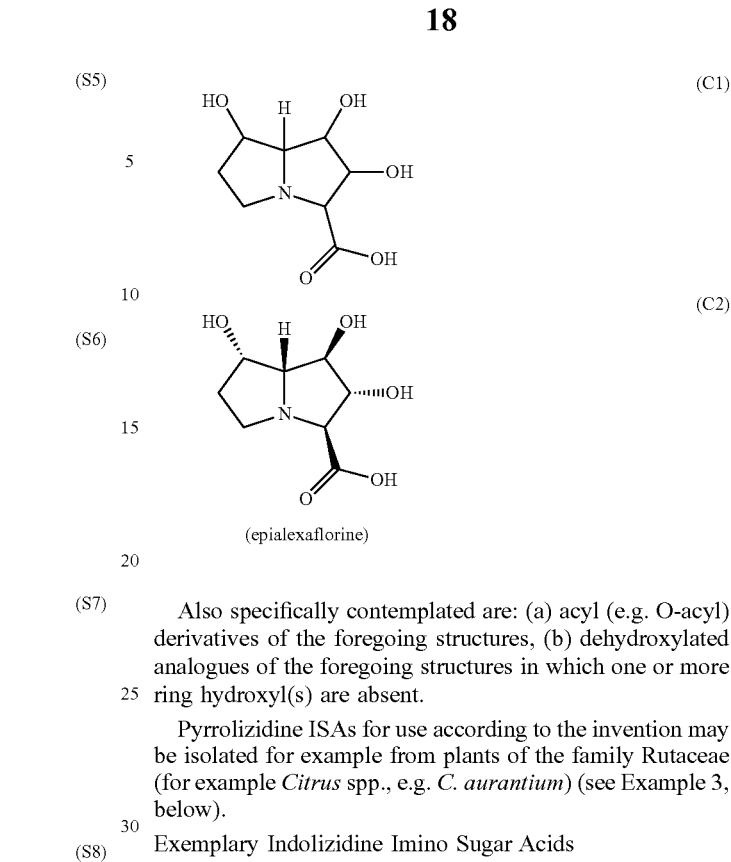

(epialexaflorine)

Also specifically contemplated are: (a) acyl (e.g. O-acyl) derivatives of the foregoing structures, (b) dehydroxylated analogues of the foregoing structures in which one or more ring hydroxyl(s) are absent.

Pyrrolizidine ISAs for use according to the invention may be isolated for example from plants of the family Rutaceae (for example *Citrus* spp., e.g. *C. aurantium*) (see Example 3, below).

Exemplary Indolizidine Imino Sugar Acids

The ISA of the invention may be an indolizidine ISA having at least 2 (preferably at least 3, 4 or 5) free hydroxyl (or hydroxyalkyl) groups on the ring system nucleus.

Exemplary indolizidine ISAs according to the invention may be selected from the structures shown below:

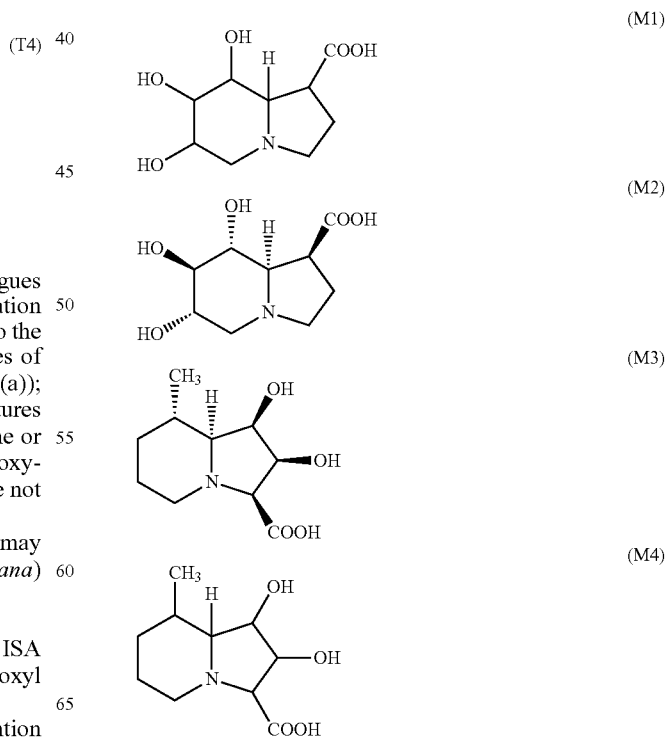

Also specifically contemplated are: (a) N-acid analogues of the foregoing structures S3 and S4 in which the location of the carboxyl group is switched from the ring carbon to the ring nitrogen, e.g. T4; (b) acyl (e.g. O-acyl) derivatives of the foregoing structures (or of the N-acid analogues of (a)); and (c) dehydroxylated analogues of the foregoing structures (or of the N-acid analogues of (a) and (b)) in which one or more ring hydroxyl(s) are absent (except that dehydroxylated analogues of the monohydroxylated S3 and S4 are not contemplated).

Pyrrolidine ISAs for use according to the invention may be isolated for example from *Stevia* spp. (e.g. *S. rebaudiana*) (see Example 2, below).

Exemplary Pyrrolizidine Imino Sugar Acids

The ISA of the invention may be a pyrrolizidine ISA having at least 2 (preferably at least 3, 4 or 5) free hydroxyl (or hydroxyalkyl) groups on the ring system nucleus.

Exemplary pyrrolizidine ISAs according to the invention may be selected from the structures shown below:

-continued

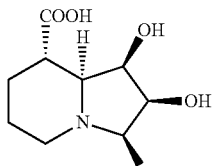
(M5)

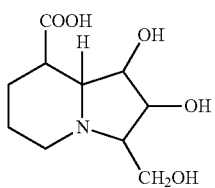
(M6)

Also specifically contemplated are: (a) acyl (e.g. O-acyl) derivatives of the foregoing structures and (b) dehydroxylated analogues of the foregoing structures in which one or more ring hydroxyl(s) are absent.

Indolizidine ISAs for use according to the invention may be isolated for example from *Citrus* species (Rutaceae), *Lotus* species, *Castanospermum* and *Alexa* species (Fabaceae); *Eugenia* and *Syzygium* species (Myrtaceae) and *Cucurbita* species (Cucurbitaceae).

Exemplary Nortropane Imino Sugar Acids

The ISA of the invention may be a nortropane ISA having at least 2 (preferably at least 3) free hydroxyl (or hydroxyalkyl) groups on the ring system nucleus. Also contemplated are N-acid derivatives of the foregoing. An exemplary nortropane ISA according to the invention has the structure shown below:

Nor-tropane ISAs for use according to the invention may be isolated for example from plants in the Solanaceae (e.g. *Solanum* and *Lycium* species) and Moraceae (Mulberry).

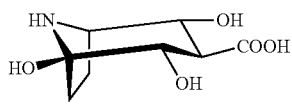
(N1)

Exemplary Ring-Open Imino Sugars

Also considered are amino sugars acids formed by the opening of the imino ring such as compound P1 and P2 (found in *Cucurbita* species) and P3. Such compounds may also be the biological precursors of the imino sugar acids.

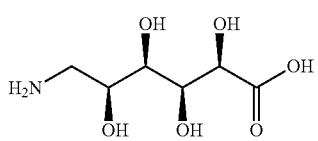
P1

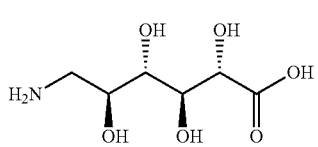
P2

-continued

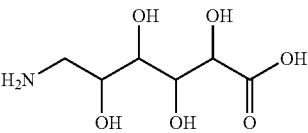
P3

Biological Activities and Functional Attributes of the ISAs of the Invention

The ISAs of the invention preferably do not inhibit glucosidase activity (or do not inhibit glucosidase activity to a clinically-significant extent). Without wishing to be bound by any theory, it is thought that the ISAs of the invention may stimulate, directly or indirectly, pancreatic β-cell activity and/or regeneration in vivo. Thus, preferred ISAs for use according to the invention stimulate, directly or indirectly, pancreatic β-cell activity and/or regeneration in vivo and improve insulin response. In such embodiments, the ISAs find particular application in the treatment of type 1 (or insulin-dependent) diabetes, since the ISA may promote functional regeneration of pancreatic β-cells (as reported for *Gymnema* extracts by Shanmugasundaram et al. (1990) Use of *Gymnema sylvestre* leaf extract in the control of blood glucose in insulin-dependent diabetes mellitus. J Ethnopharmacol. 1990 October; 30(3): 281-94).

Without wishing to be bound by any theory, the compounds may inhibit glucuronidases, iduronidase, sialidase or hexosaminidases. Reducing glucuronidase activity may for example improve beta cell function, directly or indirectly, via improved removal of toxins as glucuronides.

Compounds which stimulate pancreatic β-cell activity and/or regeneration in vivo may be readily identified by various methods known in the art, including both in vivo and ex vivo cell-based assays. For example, insulin release from isolated pancreatic beta-islet cells may be used as an index of stimulatory activity and measured according to the following method.

Spague Dawley rats are killed by cervical dislocation then the branch of the bile duct leading to the liver and the duodenal end of the duct in the pancreas clamped. Collagenase solution (type V, 50 mg/ml) is then injected into the bile duct, distending the pancreas, which is then removed and incubated for 12 minutes at 37° C. 10 ml of cold Hank's buffer is added and the suspension agitated vigorously for 1 min. After 5 minutes on ice, settled islets are washed three times using ice-cold Hank's buffer and good sized islets selected under microscrope for transfer to a perifusion apparatus (Dickinson et al. 1997. Eur J Pharmacol., 339, 69-76). Islets from several rats were pooled then twenty selected for each perifusion chamber containing oxygenated (95% O2/5% CO2) Gey & Gey buffer with 1 mg/ml bovine serum albumin and glucose. Islets are perifused for one hour in medium containing 4 mM glucose to equilibrate then perifusate collected at two minute intervals (the first five fractions being used to establish baseline insulin levels). The media in the perifusion container is then changed to one containing the test concentration of glucose and test compound with subsequent fractions being collected for a further hour. Levels of insulin released in the perifusant are then assayed using a 96-well ELISA.

Compounds for use according to the invention which improve insulin response may be readily identified by various methods known in the art, including both in vivo and ex vivo cell-based assays. For example, the ability of compounds of the invention to modulate carbohydrate tolerance can be determined by the following in vivo assay in lean mice as a model.

Male ddy (29-33 g) or C57BL/6J (4-6 weeks) mice are fasted overnight and then used for acute carbohydrate loading tests. Glucose (2.5 g/kg body weight), maltose (2.5 g/kg body weight), sucrose (2.5 g/kg body weight), isosucrose (2.5 g/kg body weight) or starch (1 g/kg body weight) as well as the test compounds were dissolved in 0.9% NaCl solution and administered to mouse via stomach tube. A control group is loaded with saline only. Blood samples are taken from the tail vein into lithium heparinised tubes and plasma separated by centrifugation both preloading and at various times post loading. Plasma glucose and insulin are measured using commercially available kits.

Compounds having particular utility in the treatment of obesity may be readily identified by various methods known in the art, including both in vivo and ex vivo cell-based assays. For example, the effect of compounds of the invention in diet-induced obese mice may be determined as follows.

Male C57BL/6J (4-6 weeks) mice are allowed free access to a high fat diet (45% kcal obtained from fat, Research Diets USA) and water. After 7 days acclimatization, mice were dosed in groups of ten mice orally with different concentrations of test compound or vehicle for 32 days. Both a fed and fasted carbohydrate test using glucose is performed at 28 days with plasma glucose and insulin measured. All animals are then returned to a normal diet. At the end of the experiment, plasma glucose, insulin, triglycerides, cholesterol is measured. Body fat, protein, water and ash levels of the carcasses are also measured using standard chemical analysis techniques (Dickinson et al 2001. Physiology and Behaviour 74, 425-433).

Compounds having particular utility in the treatment of metabolic dysfunction may be readily identified by various methods known in the art, including both in vivo and ex vivo cell-based assays. For example, db/db mice can be used as a chronic model of metabolic dysfunction, as described below.

db/db mice obtained from Jackson Labs were allowed 14 days acclimatisation with access to standard laboratory chow and water where body weight is monitored prior to experimentation. Basel levels of plasma glucose and insulin as well as HbA1c are measured to allow group assignment and then animals are dosed in groups of twelve mice orally with different concentrations of test compound or vehicle for 6 weeks. Daily measurements of food and water intake as well as bodyweight are taken with HbA1c monitored weekly. Both a fed and fasted carbohydrate test using glucose is performed at different points in the experiment with plasma glucose and insulin measured.

Chemical Synthesis

The ISAs described herein may be made by conventional methods. Methods of making heteroaromatic ring systems are well known in the art. In particular, methods of synthesis are discussed in Comprehensive Heterocyclic Chemistry, Vol. 1 (Eds.: A R Katritzky, C W Rees), Pergamon Press, Oxford, 1984 and Comprehensive Heterocyclic Chemistry II: A Review of the Literature 1982-1995 The Structure, Reactions, Synthesis, and Uses of Heterocyclic Compounds, Alan R. Katritzky (Editor), Charles W. Rees (Editor), E. F. V. Scriven (Editor), Pergamon Pr, June 1996. Other general resources which would aid synthesis of the compounds of interest include March's Advanced Organic Chemistry: Reactions, Mechanisms, and Structure, Wiley-Interscience; 5th edition (Jan. 15, 2001). Some exemplary synthetic schemes for producing ISAs for use according to the invention are shown below:

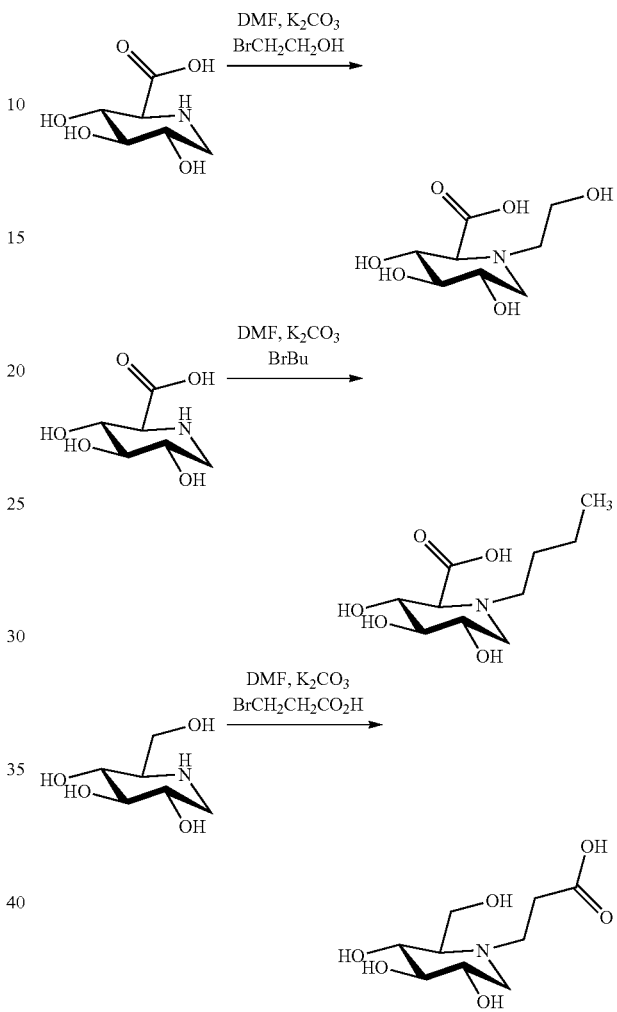

Further relevant information may be found in the following references, the content of which is incorporated herein by reference:

Synthesis of 2S-carboxy-3R,4R,5S-trihydroxypiperidine, a naturally occurring inhibitor of β-D-glucuronidase. Bernotas, Ronald C.; Ganem, Bruce. Dep. Chem., Cornell Univ., Ithaca, N.Y., USA. Tetrahedron Letters (1985), 26(41), 4981-2

Enantiospecific syntheses of 2S,3R,4R,5S-trihydroxypipecolic acid, 2R,3R,4R,5S-trihydroxypipecolic acid, 2S,4S, 5S-dihydroxypipecolic acid, and bulgecinine from D-glucuronolactone. Bashyal, B. P.; Chow, H. F.; Fleet, G. W. J. Dyson Perrins Lab., Oxford Univ., Oxford, UK. Tetrahedron Letters (1986), 27(27), 3205-8.

The synthesis of polyhydroxylated amino acids from glucuronolactone:
enantiospecific syntheses of 2S,3R,4R,5S-trihydroxypipecolic acid, 2R,3R,4R,5S-trihydroxypipecolic acid and 2R,3R,4R-dihydroxyproline. Bashyal, Bharat P.; Chow, Hak Fun; Fellows, Linda E.; Fleet, George W. J. Dyson Perrins Lab., Oxford Univ., Oxford, UK. Tetrahedron (1987), 43(2), 415-22.

Synthesis of deoxymannojirimycin, fagomine, and deoxynojirimycin, 2-acetamido-1,5-imino-1,2,5-trideoxy-D-mannitol, 2-acetamido-1,5-imino-1,2,5-trideoxy-D-glucitol, 2S,3R,4R,5R-trihydroxypipecolic acid and 2S,3R,4R,5S-trihydroxypipecolic acid from methyl 3-O-benzyl-2,6-dideoxy-2,6-imino-α-D-mannofuranoside. Fleet, George W. J.; Fellows, L. E.; Smith, Paul W. Dyson Perrins Lab., Oxford Univ., Oxford, UK. Tetrahedron (1987), 43(5), 979-90.

Preparation of 2-carboxy-3,4,5-trihydroxypiperidines as allergy inhibitors, antiarthritics, and for control of mucous production. Lockhoff, Oswald; Hayauchi, Yutaka. (Bayer A.-G., Fed. Rep. Ger.). Ger. Offen. (1988), 16 pp. CODEN: GVVXXBX DE 3628486 A1 19880225 Patent written in German.

Synthesis of aza sugars as potent inhibitors of glycosidases. Le Merrer, Yves; Poitout, Lydie; Depezay, Jean-Claude; Dosbaa, Isabelle; Geoffroy, Sabine; Foglietti, Marie-Jose. Laboratoire de Chimie et Biochimie Pharmacologiques et Toxicologiques, Universite Rene Descartes, associe au CNRS, Paris, Fr. Bioorganic & Medicinal Chemistry (1997), 5(3), 519-533.

A new asymmetric synthesis of (2S,3R,4R,5S)-trihydroxyipecolic acid. Tsimilaza, Andriamihamina; Tite, Tony; Boutefnouchet, Sabrina; Lallemand, Marie-Christine; Tillequin, Francois; Husson, Henri-Philippe. Laboratoire de Pharmacognosie, Faculte des Sciences Pharmaceutiques et Biologiques, UMR 8638 Associee au CNRS, l'Universite Paris-Descartes, Paris, Fr. Tetrahedron: Asymmetry (2007), 18(13), 1585-1588.

Synthesis of both enantiomers of hydroxyipecolic acid derivatives equivalent to 5-azapyranuronic acids and evaluation of their inhibitory activities against glycosidases. Yoshimura, Yuichi; Ohara, Chiaki; Imahori, Tatsushi; Saito, Yukako; Kato, Atsushi; Miyauchi, Saori; Adachi, lsao; Takahata, Hiroki. Faculty of Pharmaceutical Sciences, 4-4-1, Komatsushima, Tohoku Pharmaceutical University, Aoba-ku, Miyagi, Sendai, Japan. Bioorganic & Medicinal Chemistry (2008), 16(17), 8273-8286.

Purification from Botanic Sources

The ISAs described herein may be isolated from natural sources. For example, plant material from the following botanic sources may be used as starting material for the isolation and purification of the ISAs for use according to the invention: *Stevia, Gymnema, Citrus, Andrographis paniculata, Lycium* species, leguminous spp. e.g. *Aspalanthus linearis* (Rooibos), *Glycine max, Lotus* species and *Castanospermum australe* (Fabaceae) and Cucurbitaceae species. The ISAs of the invention are water-soluble and can be concentrated by anion exchange chromatography or cation exchange chromatography. Size exclusion methods can also be used to concentrate them. Thus, it will be appreciated that those skilled in the art can readily purify and isolate the ISAs of the invention using standard techniques.

Medical Applications

The invention finds broad application in the treatment of any energy utilization disease.

Thus, diseases which may be treated according to the invention include, for example, disorders of homeostasis, metabolic diseases, dysfunction of sugar metabolism and appetite disorders.

In preferred embodiments, the invention finds application in the treatment of insulin resistance, various forms of diabetes, metabolic syndrome, obesity, wasting syndromes (for example, cancer associated cachexia), myopathies, gastrointestinal disease, growth retardation, hypercholesterolemia, atherosclerosis and age-associated metabolic dysfunction.

The invention may also be used for the treatment of conditions associated with metabolic syndrome, obesity and/or diabetes, including for example hyperglycaemia, glucose intolerance, hyperinsulinaemia, glucosuria, metabolic acidosis, cataracts, diabetic neuropathy, diabetic nephropathy, diabetic retinopathy, macular degeneration, glomerulosclerosis, diabetic cardiomyopathy, insulin resistance, impaired glucose metabolism, arthritis, hypertension, hyperlipidemia, osteoporosis, osteopenia, bone loss, brittle bone syndromes, acute coronary syndrome, infertility, short bowel syndrome, chronic fatigue, eating disorders, intestinal motility dysfunction and sugar metabolism dysfunction.

The invention may also be used to suppress appetite.

Particularly preferred is the treatment of insulin resistance, metabolic syndrome, obesity and diabetes (particularly type 2 diabetes).

Insulin Resistance, Metabolic Syndrome and Diabetes

The invention finds application in the treatment of insulin resistance. Insulin resistance is characterized by a reduced action of insulin in skeletal muscle, adipocytes and hepatocytes so that normal amounts of insulin become inadequate to produce a normal insulin response from the cells of these tissues. In adipocytes, insulin resistance results in hydrolysis of stored triglycerides, leading to elevated free fatty acids in the blood plasma. In muscle, insulin resistance reduces glucose uptake while in hepatocytes it reduces glucose storage. In both of the latter cases an elevation of blood glucose concentrations results. High plasma levels of insulin and glucose due to insulin resistance often progresses to metabolic syndrome and type 2 diabetes.

The invention finds application in the treatment of metabolic syndrome (as herein defined). The disorder is also known as (metabolic) syndrome X, insulin resistance syndrome, Reaven's syndrome and CHAOS.

The invention finds application in the treatment of diseases associated with metabolic syndrome, including for example: fatty liver (often progressing to non-alcoholic fatty liver disease), polycystic ovarian syndrome, hemochromatosis (iron overload) and acanthosis nigricans (dark skin patches).

The invention finds application in the treatment of Type 2 diabetes. Type 2 diabetes is a chronic disease that is characterised by persistently elevated blood glucose levels (hyperglycaemia). Insulin resistance together with impaired insulin secretion from the pancreatic β-cells characterizes the disease. The progression of insulin resistance to type 2 diabetes is marked by the development of hyperglycaemia after eating when pancreatic β-cells become unable to produce adequate insulin to maintain normal blood sugar levels (euglycemia)).

The invention finds application in the treatment of Type 1 diabetes (or insulin dependent diabetes). Type 1 diabetes is characterized by loss of the insulin-producing beta cells of the islets of Langerhans in the pancreas, leading to a deficiency of insulin. The main cause of this beta cell loss is a T-cell mediated autoimmune attack. There is no known preventative measure that can be taken against type 1 diabetes, which comprises up to 10% of diabetes mellitus cases in North America and Europe. Most affected people are otherwise healthy and of a healthy weight when onset occurs. Sensitivity and responsiveness to insulin are usually normal, especially in the early stages.

Thus, the invention finds broad application in the treatment and/or prophylaxis of metabolic syndrome and/or diabetes (including type 1 and type 2 diabetes and insulin resistance), including in particular obesity (especially central obesity) and elevated serum triglyceride levels.

These medical applications may be applied to any warm-blooded animal, including humans. The applications include veterinary applications, wherein the ISAs are administered to non-human animals, including primates, dogs, cats, horses, cattle and sheep.

Herbal Quality Control Aspects
Food Additive Samples

The food additive samples used in the methods of the present invention may be dried plant material or aliquots of the herbal food additive in the form in which it is added to foodstuffs and beverages. Alternatively, the samples may be pre-processed in any of a wide variety of ways prior to characterization. Pre-processing may involve physical or chemical pre-processing, for example powdering, grinding, freezing, evaporation, filtration, pressing, spray drying, extrusion, supercritical solvent extraction and tincture production.

Preferably, the food additive sample is fractionated prior to characterization. Any suitable method of fractionation may be employed, including solvent extraction(s). In a preferred embodiment the sample is fractionated by: (a) ion-exchange chromatography to produce an extract enriched in polar compounds and a non-polar residue; and then (b) chromatographic fractionation of the enriched extract of step (a) to yield one or more polar fractions comprising one or more polar phytochemical(s). In such embodiments the chromatographic fractionation preferably comprises gas-liquid chromatography (GC), for example GC-MS. When GC is used, the enriched extract may be derivatized prior to chromatography.

In cases where the herbal food additive is administered or sold in the form of a whole plant (or part thereof), the plant material may be dried prior to use. Any convenient form of drying may be used, including freeze-drying, spray drying or air-drying.

Detection of Imino Sugar Acids and Imino Sugars

Any suitable form of characterization of the food additive sample may be employed, including without limitation functional and/or physical and/or chemical characterization, sufficient to detect the presence or absence or measure the amount of imino sugar acid/imino sugar in the sample.

Where the samples are physically characterized, the characterization may be selected from: (a) quantification of the phytochemical component(s); and/or (b) measurement of the purity of the constituents; and/or (c) determination of molecular weight (or molecular weight distribution or various statistical functions thereof in the case of fractions which comprise a plurality of different phytochemical constituents); and/or (d) determination of the molecular formula (e) (e.g. by nuclear magnetic resonance); and/or (e) spectral analysis.

Spectral analysis is particularly preferred, and may produce any or all of the following spectra:
  (a) mass spectra (e.g. the mass to charge (m/z) value versus abundance), and/or
  (b) chromatographic data (e.g. spectra, column retention times, elution profiles etc), and/or
  (c) photodiode array (PDA) spectra (e.g. in both UV and visible ranges), and/or
  (d) electrochemical detection
  (e) nuclear magnetic resonance (NMR) spectra (e.g. spectral data sets obtained via $^1$H and/or $^{13}$C NMR).

When used according to the invention, the spectral analysis may be coupled with fractionation of the sample, for example by use of GC-MS and/or HPLC-PDA-MS.

Particularly preferred is the use of GC-MS to detect the presence or absence or measure the amount of imino sugar acid/imino sugar in the sample.

Where the samples are chemically characterized, the characterization may be selected from measurements of the chemical reactivity of phytochemical constituent(s), the solubility of phytochemical constituent(s), the stability and melting point of phytochemical constituent(s) or any combination thereof.

Where the samples are functionally characterized, the characterization may comprise a biological assay, for example selected from in vivo or in vitro assays, enzyme inhibition assays (for example glycosidase and/or lipase inhibition), receptor binding assays, cellular assays (e.g. cell replication, cell-pathogen, cell-cell interaction and cell secretion assays), immunoassays, anti-microbial activity (e.g. bacterial and viral cell-binding and/or replication) assays, toxicity assays (e.g. $LD_{50}$ assays) or any combination thereof.

Solvent Extractions

Suitable polar solvents for use in the process of the invention include without limitation organic solvents such as organic alcohols. Preferred are ethanol and methanol, as well as ethanol/water or methanol/water mixtures. Preferably, the polar solvent is selected from 51 to 80% ethanol/water, 31 to 50% ethanol/water, and up to 30% ethanol/water. Particularly preferred is a polar solvent which is approximately 50% ethanol/water. Suitable non-polar solvents for use in the process of the invention include without limitation organic solvents such as hexane and dichloromethane (DCM) or chloroform. Particularly preferred is dichloromethane. The conditions (time, temperature, degree of agitation etc.) under which the extraction(s) are performed can be readily determined empirically and vary according to the nature of the sample, the nature of any pre-processing and the solvent system selected.

Chromatographic Fractionation

Chromatographic fractionation may comprise gas-liquid chromatography. Gas-liquid chromatography is a process whereby a complex mixture of volatile substances is separated into its constituents by partitioning the sample between an inert gas under pressure and a thin layer of non-volatile liquid coated on an inert support inside a heated column. In order to achieve a good separation of specific compounds in a mixture, it is crucial to use a column with the correct characteristics. The nature of the solid support, type and amount of liquid phase, method of packing, overall length and column temperature are important factors.

Those skilled in the art, by routine trial and error and by using common general knowledge, will be able readily to determine the appropriate column characteristics according to the circumstances, including inter alia the extract under study and the nature of the solvent used in the extraction and the types of chemicals expected in those solvents. Particularly preferred, and useful in many circumstances, are capillary columns coated with a non-polar liquid phase (25 m×0.22 mm id×0.25 µm BPX5 stationary phase, produced by SGE Ltd., or equivalents thereof).

Many compounds are unsuitable for direct injection into a gas chromatograph because of their high polarity, low volatility or thermal instability. Compounds that are highly hydroxylated are difficult to vapourise because of intermolecular hydrogen bonding. However, by replacing the hydroxyl hydrogens with other chemical groups, they can be made sufficiently volatile for GC analysis. The two most popular means of derivatising hydroxyl groups are acetylation and silylation, where acetylates [CH$_3$CO—O—R] or silyl ethers, e.g. trimethylsilyl (TMS) ethers [(CH$_3$)$_3$Si—O—R] are formed. Thus, in embodiments where the enriched extract is chromatographically fractionated on an analytical scale the phytochemical constituents of the enriched extract are preferably derivatized, for example by acylation or silylation. Particularly preferred is trimethyl silyl (TMS) derivatization.

Chromatographic fractionation may also comprise ion exchange chromatography. Ion-exchange chromatography partially purifies ionic species to concentrate them and remove contaminating substances. Those skilled in the art, by routine trial and error and using common general knowledge, will be able readily to identify suitable column packing materials and mobile phase(s), which will depend inter alia on the quantities to be fractionated, the extracts under study and the nature of the solvent used in the extraction. Particularly preferred in the methods of the present invention are strongly acidic cation exchange resins which can be used in either the free acid or hydrogen (H$^+$) form or in the ammonium (NH$_4^+$) salt form). These forms adsorb cations from solution and release an equivalent number of counterions back into solution (either H$^+$ or NH$_4^+$ ions, depending on the form used). Also preferred are strongly basic anion exchange resins which when used in the hydroxide form (OH–) will strongly bind imino sugar acids. The imino sugar acids can then be released by the use of acids such as acetic acid (e.g. a 2M solution).

Fraction Characterization

The form the characterization takes depends on the nature of the herbal food additive under study and the characterization techniques employed. In general, any or all of the following approaches may be used:

(a) Functional Characterization

The functional characterization may comprise a biological assay. Biological assays may be carried out in vivo or in vitro, and may include enzyme inhibition assays (for example glycosidase and/or lipase inhibition). Other biological assays include receptor binding assays, cellular assays (including cell replication, cell-pathogen and cell-cell interaction and cell secretion assays), immunoassays, antimicrobial activity (e.g. bacterial and viral cell-binding and/or replication) assays and toxicity assays (e.g. LD$_{50}$ assays).

Functional characterization may also be carried out indirectly by a form of characterization which permits the identification of one or more indices of biological activity.

(b) Physical Characterization

This can take the form of quantification of the phytochemical component(s) present in any given fraction or at any other stage in the process, measurement of the purity of the constituents, determination of molecular weight (or molecular weight distribution or various statistical functions thereof in the case of fractions which comprise a plurality of different phytochemical constituents), determination of the molecular formula(e) (e.g. by nuclear magnetic resonance) and various spectral analyses.

Particularly useful spectral characteristics include:
Mass spectra (e.g. the mass to charge (m/z) value versus abundance), and/or
Chromatographic data (e.g. spectra, column retention times, elution profiles etc), and/or
Photodiode array (PDA) spectra (e.g. in both UV and visible ranges), and/or
Nuclear magnetic resonance (NMR) spectra (including spectral data sets obtained via $^1$H and/or $^{13}$C NMR).

Spectral characterization can be coupled with the fractionation step. For example, GC-MS and HPLC-PDA-MS can be used (as described herein) to couple the fractionation with the obtention of mass spectral, UV-visible spectral and chromatographic spectral data.

Any or all of the above characteristics can be used to define a "chemical fingerprint" for any given sample (or any fraction or phytochemical constituent thereof).

(c) Chemical Characterization

This can take the form of measurements inter alia of the chemical reactivity of phytochemical constituent(s), their solubility, stability and melting point.

Posology

The ISAs of the present invention can be administered by oral or parenteral routes, including intravenous, intramuscular, intraperitoneal, subcutaneous, transdermal, airway (aerosol), rectal, vaginal and topical (including buccal and sublingual) administration. Preferred is oral administration.

The amount of the ISA administered can vary widely according to the particular dosage unit employed, the period of treatment, the age and sex of the patient treated, the nature and extent of the disorder treated, and the particular ISA selected.

Moreover, the ISAs of the invention can be used in conjunction with other agents known to be useful in the treatment of metabolic syndrome and/or diabetes (including type 1 and type 2 diabetes and insulin resistance) and in such embodiments the dose may be adjusted accordingly.

In general, the effective amount of the ISA administered will generally range from about 0.01 mg/kg to 500 mg/kg daily. A unit dosage may contain from 0.05 to 500 mg of the ISA, and can be taken one or more times per day. The ISA can be administered with a pharmaceutical carrier using conventional dosage unit forms either orally, parenterally, or topically, as described below.

The preferred route of administration is oral administration. In general a suitable dose will be in the range of 0.01 to 500 mg per kilogram body weight of the recipient per day, preferably in the range of 0.1 to 50 mg per kilogram body weight per day and most preferably in the range 1 to 5 mg per kilogram body weight per day.

The desired dose is preferably presented as a single dose for daily administration. However, two, three, four, five or six or more sub-doses administered at appropriate intervals throughout the day may also be employed. These sub-doses may be administered in unit dosage forms, for example, containing 0.001 to 100 mg, preferably 0.01 to 10 mg, and most preferably 0.5 to 1.0 mg of active ingredient per unit dosage form.

Formulation

The compositions of the invention comprise the ISA of the invention, optionally together with a pharmaceutically acceptable excipient.

The ISA of the invention may take any form. It may be synthetic, purified or isolated from natural sources (for example from any of the botanic sources identified herein, including for example a botanical source selected from: (a) *Stevia* spp. (e.g. *S. rebaudiana*); (b) *Gymnema* spp. (e.g. *G. sylvestre*); (c) *Andrographis* spp. (e.g. *A. paniculata*); (d) leguminous species (e.g. *Aspalanthus* spp., *Baphia* spp., *Glycine max*, *Alexa* spp. *Castanospermum Australe*), *Lotus* Spp.; (e) Plants of the Family Rutaceae (for example *Citrus* spp., e.g. *C. aurantium*); (f) *Lycium barbarum* (Goji) and (g) plants of the Cucurbitaceae (e.g. *C. ficifolia*, Siam Pumpkin and *Momordica charantia*).

When isolated from a natural source, the ISA of the invention may be purified. However, the compositions of the invention may take the form of herbal medicines, as hereinbefore defined. Such herbal medicines preferably are analysed to determine whether they meet a standard specification prior to use.

The herbal medicines for use according to the invention may be dried plant material. Alternatively, the herbal medicine may be processed plant material, the processing involving physical or chemical pre-processing, for example powdering, grinding, freezing, evaporation, filtration, pressing, spray drying, extrusion, supercritical solvent extraction and tincture production. In cases where the herbal medicine is administered or sold in the form of a whole plant (or part thereof), the plant material may be dried prior to use. Any convenient form of drying may be used, including freeze-drying, spray drying or air-drying.

In embodiments where the ISA of the invention is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc.

The pharmaceutical compositions may take any suitable form, and include for example tablets, elixirs, capsules, solutions, suspensions, powders, granules and aerosols.

The pharmaceutical composition may take the form of a kit of parts. The kit may comprise the composition of the invention together with instructions for use and/or a plurality of different components in unit dosage form.

Tablets for oral use may include the ISA of the invention, either alone or together with other plant material associated with the botanical source(s) (in the case of herbal medicine embodiments). The tablets may contain the ISA of the invention mixed with pharmaceutically acceptable excipients, such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the ISA of the invention is mixed with a solid diluent, and soft gelatin capsules wherein the active ingredient is mixed with water or an oil such as peanut oil, liquid paraffin or olive oil. For oral administration the ISA of the invention can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment, the ISAs of the invention are tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, colouring agents, and flavouring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The ISAs of the invention may also be administered parenterally, that is, subcutaneously, intravenously, intramuscularly, or interperitoneally.

In such embodiments, the ISA is provided as injectable doses in a physiologically acceptable diluent together with a pharmaceutical carrier (which can be a sterile liquid or mixture of liquids). Suitable liquids include water, saline, aqueous dextrose and related sugar solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carhomers, methylcellulose, hydroxypropylmethylcellulose, or carboxymethylcellulose), or emulsifying agent and other pharmaceutically adjuvants. Suitable oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil.

Suitable fatty acids include oleic acid, stearic acid, and isostearic acid. Suitable fatty acid esters are, for example, ethyl oleate and isopropyl myristate.

Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the ISA of the invention in solution. Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

When used adjunctively, the ISAs of the invention may be formulated for use with one or more other drug(s). In particular, the ISAs of the invention may be used in combination with anti-diabetic agents (as herein described).

For example, the ISAs of the invention may be used with anti-diabetic agents selected from the following drug classes: biguanide, sulfonylurea, thiazolidinediones, α-glucosidase inhibitors, meglitinides, peptide analogs, dipeptidyl peptidase-4 (DPP-4) inhibitors and amylin agonist. Adjunctive use may be reflected in a specific unit dosage designed to be compatible (or to synergize) with the other drug(s), or in formulations in which the ISA is admixed with one or more anti-diabetic agent(s) (or else physically associated with the other agent(s) within a single unit dose). Adjunctive uses of the ISAs of the invention may also be reflected in the composition of the pharmaceutical kits of the invention, in which the ISA of the invention is co-packaged (e.g. as part of an array of unit doses) with the anti-diabetic drug(s). Adjunctive use may also be reflected in information and/or instructions relating to the co-administration of the ISA with anti-diabetic drug(s).

The ISAs of the invention may also be formulated as nutraceuticals forming part of a beverage or foodstuff.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1

Detection of the Compound of Formula (G2) in *Gymnema*

*Gymnema sylvestre* is a liana or climbing plant with stems up to 8 m in length. It grows in open woods and bushland at an altitude of 100-1000 m in India, China, Indonesia, Japan, Malaysia, Sri Lanka, Vietnam and South Africa: Both the leaf and root are used in Ayurvedic medicine. Because of its property of abolishing the taste of sugar it was given the Hindi names of Gurmar and Madhunashini meaning 'sugar destroying.' The herb is traditionally used for the treatment of metabolic syndrome and *Gymnema* extracts are sold in Japan for the control of obesity.

A controlled study on insulin-dependent diabetics found that a water-soluble *Gymnema* extract (400 mg/day) reduced insulin requirements (by about 50%) (Shanmugasundaram et al. (1990), J Ethnopharmacol. 30:281-294). Over the duration of treatment *Gymnema* lowered fasting mean blood glucose (by about 35%), glycosylated haemoglobin and glycosylated plasma protein levels from baseline values. Cholesterol was significantly reduced and brought to near normal levels. Triglycerides, free fatty acids and serum amylase were also lowered. The treatment period ranged from 6-30 months. The significant decrease in glycosylated haemoglobin occurred after 6-8 months of *Gymnema* treatment but remained significantly higher than normal values. None of these reductions was observed in control patients on insulin therapy alone who were studied over a period of 10-12 months. The authors suggested that *Gymnema* enhanced endogenous insulin production, possibly by pancreatic regeneration, as levels of C-peptide, a by-product of the conversion of proinsulin to insulin, were apparently raised (in comparison to both the insulin alone group and normal subjects).

A second study by the same research group found that the same *Gymnema* preparation (400 mg/day) produced similar results for non-insulin-dependent diabetics (Baskaran et al. (1990) J Ethnopharmacol. 30:295-300). Fasting blood glucose, glycosylated haemoglobin and glycosylated plasma protein were significantly reduced compared to baseline values (p<0.001) after 18-20 months of treatment. None of these reductions was observed in patients receiving conventional therapy alone who were studied over a period of 10-12 months. By the end of the treatment period cholesterol, triglycerides, phospholipids and free fatty acid levels were also significantly reduced compared to baseline values in those receiving *Gymnema* (p<0.001). Control patients receiving only conventional therapy achieved reductions in cholesterol, triglycerides and free fatty acids (p<0.05-p<0.001). Fasting and post-prandial serum insulin levels were significantly increased in the *Gymnema* group compared to those taking only conventional drugs (p<0.01). Twenty-one of the 22 patients were able to reduce their intake of hypoglycaemic drugs; 5 of these discontinued hypoglycaemic drugs entirely and maintained their blood glucose homeostasis with *Gymnema* extract alone. The authors' suggestion of beta cell regeneration or repair facilitated by *Gymnema* was supported by the higher insulin levels in the serum of patients after *Gymnema* supplementation. *Gymnema* administration to healthy volunteers did not produce any acute reduction in fasting blood glucose level.

The trace shown in FIG. 1(a) is the GC-MS chromatogram of *Gymnema* water extract showing the compound of formula (G2) (trimethylsilyl derivative) as a major component at 9.26 minutes after removal of sugars.

Example 2

Uptake of G2 after Oral Administration of *Gymnema Sylvestre*

In a preliminary experiment on one male volunteer to determine if G2 was readily absorbed from the gastrointestinal tract, a water extract of *Gymnema* leaves obtained commercially containing 7 mg of G2 was drunk and urine monitored for G2 over 4 hours (0-2 hours and 2-4 hours). An internal standard of 1 mg of castanospermine was added to the two samples of urine prior to applying to a cation exchange resin (IR120 in the $H^+$ form). After washing the resin with copious water, the bound material was displaced using excess 2M $NH_4^+$ solution and dried for GC-MS analysis. The samples were derivatised using Pierce Tri-Sil to produce trimethyl-silyl-derivatives of the imino sugars and imino sugar acids. GC-MS was carried out on a Perkin Elmer TurboMass Gold mass spectrometer, with a quadrupole ion filter system, which was run at 250° C. constantly during analysis. The detector mass range was set to 100 to 650 amu. The temperature of the transfer line (GC to MS) was held at 250° C. The GC column was a high polarity fused-silica column (Varian 'Factor Four' VF-5 ms column, 25 m×0.25 mm i.d., 0.25 μm phase thickness). The carrier gas (helium) flow rate was 1 ml min-1. G2 gives a characteristic mass spectrum as the tms derivative and was well resolved allowing quantification.

The G2 was detected in the urine at both time periods and the 7 mg appeared to be recovered within the four hours.

Figure 1B:
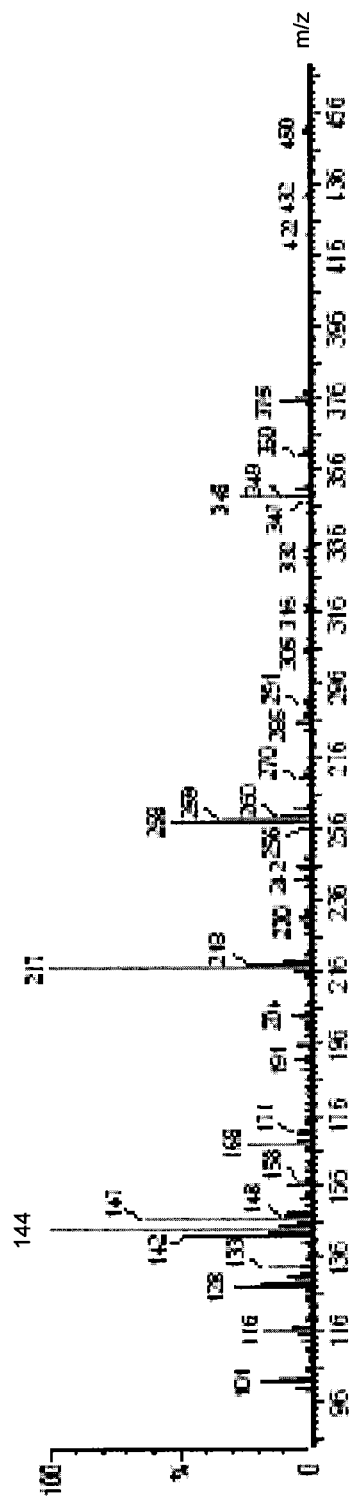

The characteristic mass spectrum (tms) of imino sugar acid G2 is shown in FIG. 1(b).

Example 3

Detection of ISAs in *Stevia rebaudiana*

*Stevia rebaudiana* (Asteraceae) is well known to contain sweeteners called steviosides and related compounds. *Stevia* has shown promise in medical research for treating such conditions as obesity and high blood pressure. Steviol glycosides have been reported to have a negligible effect on blood glucose (e.g. see Barriocanal L A et al., 2008, Regul. Toxicol. Pharmacol. 51:37-41). Stevioside has been shown to induce antihyperglycaemic, insulinotropic and glucagonostatic effects in vivo in rats in several studies. However, the steviosides themselves have been reported to have possible mutagenic activity and hence fractionating *Stevia*-derived material to remove steviosides could improve the products for anti-diabetic or obesity use.

Figure 1C:
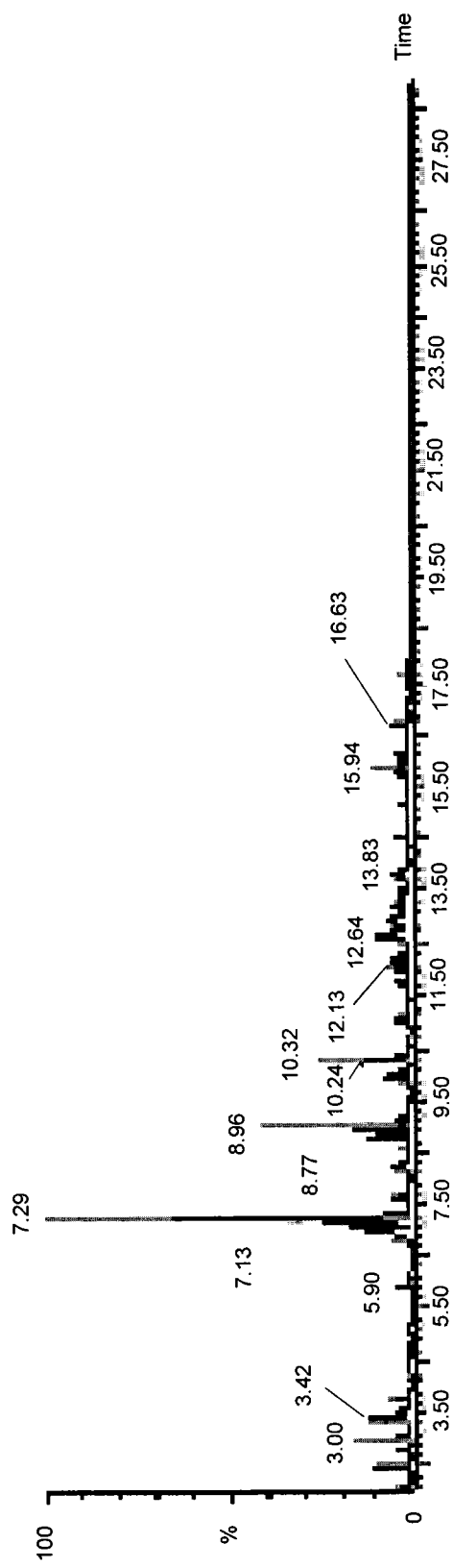

The trace shown in FIG. 1(c) is the GC-MS chromatogram of water extract of *Stevia rebaudiana* after removal of sugars showing several imino sugar acids and one imino sugar at 7.29 minutes (DMDP).

The major imino sugar acids in *S. rebaudiana* are novel pyrrolidines such as those shown below. The acid carbon chain length on the nitrogen is also observed to be longer than that shown with addition of 14 mass units ($CH_2$) noted in mass spectra of the parent compounds identified. Also present are piperidines structurally related to 1-deoxynojirimycin such as shown in structures T1 and G6. O-butyl forms of the compounds also exist in Stevia although these carbon chain lengths might also vary. The imino sugar DMDP is the compound S2 without the acid on the nitrogen.

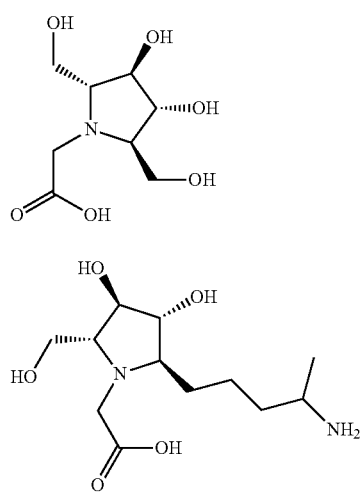

(S2)

(S6)

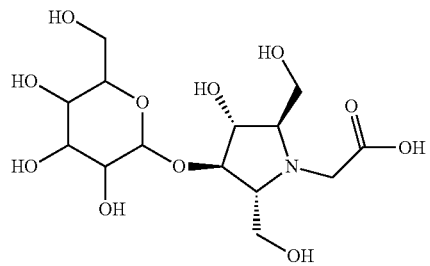

(S8)

Example 4

Detection of ISAs in *Citrus* Spp

*Citrus* species (Rutaceae) contain piperidine imino sugar acids related to the compound of formula (G2) with novel N- and O-butyl-derivatives but also appear to always contain pyrrolizidine acids such as the compound of formula (C1) shown above (epialexaflorine). This ISA was first isolated from *Alexa* species (Leguminosae) (Pereira et al. (1991): Isolation of 7a-epialexaflorine from leaves of *Alexa grandiflora*—a unique pyrrolizidine amino acid with a carboxylic acid substituent at C-3. Tetrahedron 47 (29): 5637-5640). The pyrrolizidine acid appears to be ubiquitous in *Citrus* species. *Citrus* spp. contain low levels of the imino sugar acids in comparison to *Gymnema* and *Stevia*. Bitter orange (*Citrus aurantium*) in China and grapefruit have anecdotal claims for antidiabetic or weight control uses. The ISA S9 was found to be a more major component of Bitter Oranges than C1.

Example 5

Inhibition of Glycosidases by ISAs

The results tabulated below were obtained using commercially available glycosidases and p-nitrophenyl-substrates using standard methods described for example by Watson et al (1997) *Phytochemistry* 46 255-259. All enzymes and substrates were bought from Sigma. Enzyme and substrate solutions were made using sodium phosphate buffers at the pH optima values. The enzymes used were α-D-glucosidase *Saccharomyces cerevisiae*, *Bacillus stearothermophilus*, *Oryzae sativa*), β-D-glucosidase (Almond), α-D-mannosidase (Jack bean), α-D-galactosidase (Green coffee beans), β-D-galactosidase (Bovine liver), α-L-fucosidase (Bovine kidney), N-acetyl-β-D-glucosaminidase (Bovine kidney, Jack bean, *Aspergillus oryzae*), Naringinase (*Penicillium decumbens*) and amyloglucosidase (*Aspergillus niger*). All enzymes were used with the appropriate p-nitrophenyl substrates (5 mM). Amyloglucosidase activity was measured using amylopectin (0.1%) (Merck) mixed with sodium phosphate buffer, pH 4.5 in a glass bottle, and heated in a boiling water bath for 20 minutes to dissolve with released glucose measured using Trinder glucose detection solution (Sigma).

Of particular interest is the ability of acids of the imino sugar glucosidase inhibitors such as DAB (1,4-dideoxy-1,4-imino-D-arabinitol) and DNJ (1-deoxynojirimycin) to inhibit the mammalian hexosaminidase which the parent compounds do not. Elevated levels of this enzyme activity has been shown to occur in urine of diabetic patients (Yamanouchi et al. (1998) Diabetes care 21: 619-624) but it may be that the inhibition of the enzyme activity helps to control metabolic disturbances seen in diabetics. The inhibition of the alpha-glucosidases is also reduced by addition of the acid substituent to the imino sugars (DMDP, DAB and DNJ).

| Assay | N-ethanoic-DMDP S2 | N-propanoic-DNJ T1 | N-butyl-2-butylester of G2 T2 | N-hydroxyethyl-G2 T3 | N-ethanoic-DAB T4 | N-ethanoic-DNJ G6 |
|---|---|---|---|---|---|---|
| α-D-glucosidase (Yeast) | NI | NI | NI | NI | NI | NI |
| α-D-glucosidase (*Bacillus*) | 92.7 *51.7 uM* | NI | NI | NI | NI | NI |
| α-D-glucosidase (Rice) | NI | 99.1 *2.4 uM* | NI | 67.2 *259 uM* | NI | 99.7 *1.0 uM* |
| β-D-glucosidase (Almond) | 55 | NI | NI | NI | NI | NI |
| α-D-galactosidase Green coffee bean | NI | NI | NI | NI | NI | NI |
| β-D-galactosidase Bovine liver | 60 | NI | NI | NI | NI | NI |
| α-L-fucosidase Bovine kidney | NI | NI | NI | NI | NI | NI |
| α-D-mannosidase Jack bean | NI | NI | NI | NI | NI | NI |
| β-D-mannosidase *Cellullomonas fimi* | NI | NI | NI | NI | NI | NI |
| Naringinase *Penicillium decumbens* | NI | NI | NI | NI | NI | NI |
| N-acetyl-β-D-glucosaminidase (Bovine kidney) | NI | 86.1 *32.2 uM* | NI | 82.0 *12.2 uM* | 81.9 *39.6 uM* | 83.6 *10.4 uM* |
| N-acetyl-β-D-glucosaminidase (Jack bean) | NI | NI | NI | NI | NI | NI |
| N-acetyl-β-D-glucosaminidase (*A. oryzae*) | NI | NI | NI | NI | NI | NI |
| Amyloglucosidase *Aspergillus niger* | NI | 53 | NI | NI | NI | NI |
| β-Glucuronidase Bovine liver | *507 uM* | *50 uM* | *280 uM* | *60 uM* | *160 uM* | *80 uM* |

% inhibition with compounds tested at 0.8 mM.
NI = less than 50% inhibition at top concentration
Italics = IC$_{50}$ (the concentration of compound giving 50% inhibition of the enzyme)

Of particular interest was the ability of imino sugar acids to inhibit β-Glucuronidase. The assay involved the use of Bovine liver β-glucuronidase using p-nitrophenyl β-D-glucuronide purchased from Sigma. The enzyme was assayed at 27° C. in 0.1 M citric acid/0.2M disodium hydrogen phosphate buffer at pH 5.0. The incubation mixture consisted of 10 µl of 3000 units/ml enzyme solution, 10 µl of 1 mg/ml aqueous inhibitor solution and 50 µl of 5 mM para-nitrophenyl β-D-glucuronide made up in buffer at pH 5.0. The reactions were stopped by adding 70 µl of 0.4M glycine (pH 10.4) during the exponential phase of the reaction, which had been determined at the beginning using uninhibited assays in which water replaced inhibitor. Final absorbances were read at 405 nm using a Versamax microplate reader (Molecular Devices). Assays were carried out in triplicate, and the values given were means of the three replicates per assay. Results are expressed above as IC$_{50}$ values (the concentration of the compound giving 50% inhibition of the enzyme activity. The controls contained water in place of the inhibitor.

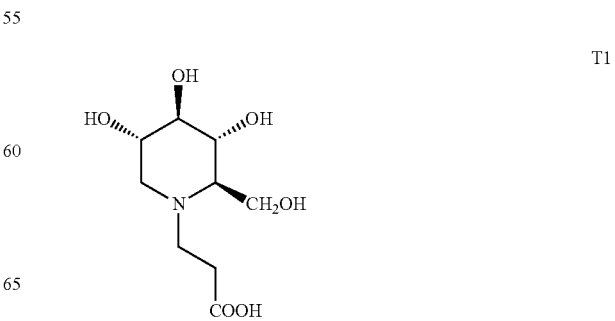

T1

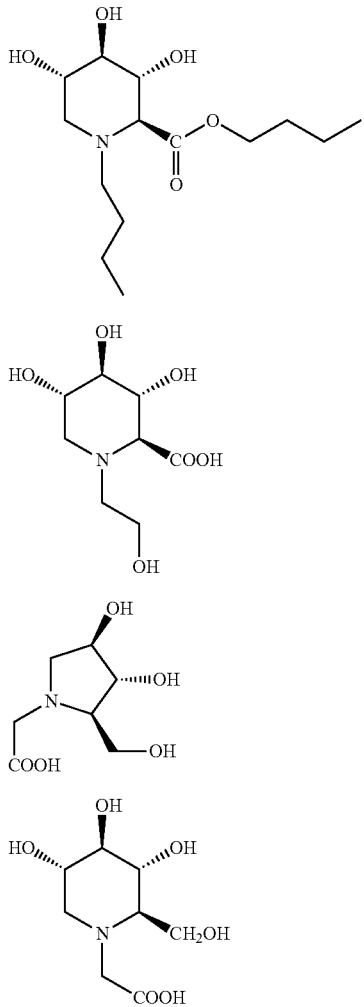

Example 6

Inhibition of Glycosidase Enzymes by the Compound of Formula (G2)

DNJ is a potent inhibitor of a wide range of α-glucosidases and inhibits digestive glucosidases with Ki values in the low or sub-µM range (Watson et al., 2001). Anti-diabetic drugs (Glyset and Miglitol) were derived from DNJ by Bayer and these function by reducing uptake of glucose into the blood but they also have side effects such as disturbance of the digestive tract. In contrast G2 is a very weak inhibitor of α-glucosidases only just reaching 50% inhibition at nearly mM concentration and so is unlikely to function in the same way. G2 has also been reported to be a weak inhibitor of glucuronidase and iduronidase (Booth et al. (2007) Acta Crystallographica Section E63, o3783-o3784 and references therein). It is not clear if inhibition of these enzymes could be involved in weight control or control of metabolic syndrome. The imino sugar fagomine has been shown to potentiate insulin release but the mechanism is unknown and might be via glucosidase inhibition (Taniguchi et al. (1998) Horm. Metab. Res. 30: 679-683). Although there is interest in compounds such as DNJ and fagomine as potential anti-diabetic agents, it may well be that the glucosidase inhibition is in fact not important for some of the in vivo anti-diabetic activity of these imino sugars; formation of small amounts of the acids in vivo may result in compounds showing glucuronidase inhibition. Without wishing to be bound by any theory, inhibition of the glucuronidase activity elevated in metabolic syndrome may aid removal of toxins and improve regulation of metabolism generally and specifically beta cell function and growth.

| Assay | DNJ | Cmpd of formula (G2) |
|---|---|---|
| α-D-glucosidase (Yeast) | 36 | NI |
| α-D-glucosidase (*Bacillus*) | 100 *2 uM* | 49 |
| α-D-glucosidase (Rice) | 100 *0.9 uM* | 55 |
| β-D-glucosidase (Almond) | NI | NI |
| α-D-galactosidase Green coffee bean | NI | NI |
| β-D-galactosidase Bovine liver | NI | NI |
| α-L-fucosidase Bovine kidney | NI | NI |
| α-D-mannosidase Jack bean | 26 | 29 |
| β-D-mannosidase *Cellullomonas fimi* | NI | NI |
| Naringinase *Penicillium decumbens* | 20 | NI |
| N-acetyl-β-D-glucosaminidase (Bovine kidney) | NI | NI |
| N-acetyl-β-D-glucosaminidase (Jack bean) | NI | 10 |
| N-acetyl-β-D-glucosaminidase (*A. oryzae*) | NI | NI |
| Amyloglucosidase *Aspergillus niger* | 32 | NI |
| β-Glucuronidase Bovine liver | NI | 90 *107 uM* |

% inhibition of compounds tested at 0.8 mM
Italics = $IC_{50}$
NI = no inhibition

Example 7

Increase in Plasma Insulin Levels In Vivo by the Compound of Formula (G2)

The study started with 42 male ob/ob mice, 10 weeks of age. The mice were fed a normal chow diet during the whole study. After 1 week of acclimatization, mice were matched on basis of body weight, plasma glucose and insulin (after 4 h-fasting) and divided in 3 groups of 10 animals (t=0 days). For the next 6 days, mice received vehicle (control group 1) or 5 mg/kg/day (group 2) or 50 mg/kg/day (group 3) of the compound of formula (G2) (test compound) around 12.00 h by gavage (5 ml/kg mouse). On the 7th day, mice were fasted at 8.00 h and received the last gavage (vehicle for group 1 or 5 mg/kg/day, test compound for group 2 or 50 mg/kg/day test compound for group 3) at 12.00 h. At 13.00 h the mice subsequently received a glucose bolus (2 g/kg mouse, 5 ml/kg mouse) by gavage as start of the oral glucose tolerance test (OGTT). Measurement of blood glucose and plasma collection was at t=0 (just before gavage of glucose) and at t=5, 15, 30, 45, 60 and 120 min after glucose bolus.

After the OGTT, mice were sacrificed with CO2 and additional blood was collected in heparin-coated tubes via heart puncture (>100 μl plasma was obtained) and heparin-plasma samples were analysed.

On day 0 mice were randomized on body weight and 4 h fasted plasma glucose and insulin levels (table 3.1.a). Twelve out of 42 mice were excluded, to create more homogenous groups with respect to body weight, plasma glucose and insulin.

Both body weight (FIG. 3.2.1) and food intake (FIG. 3.2.2) were not significantly changed after treatment with 5 mg/kg/day or 50 mg/kg/day G2, when compared to the control (vehicle) group.

When compared to the control group, plasma insulin levels at 0 min (just before the oral load of glucose) seemed to be reduced somewhat in both test compound treatment groups, although this reduction was not significant. No significant changes were seen between 3 groups at 15, 30, 45 and 60 min. Two hours after the glucose bolus, plasma insulin concentrations were significantly increased in the 5 mg/kg and the 50 mg/kg test compound treated groups when compared to the control group.

The data showed that plasma insulin levels were significantly increased in both test compound treatment groups 120 min after the oral bolus of glucose, possibly as a result of an improved pancreatic β-cell function.

Example 8

Properties of the Compound of Formula (G2)

Chemical Properties

The compound of formula (G2) is an ISA of molecular weight 177. It is freely soluble in water. The compound is stable under all normal laboratory storage conditions.

Occurrence and Exposure Data

The compound of formula (G2) is a natural product that occurs in polar extracts of a range of plants that are known in Ayurveda and the European plant pharmacopoeia. The present inventors have detected the compound at concentrations ca. 0.2 mg/mL in several herbal medicinal products used in the management of obesity and diabetes in humans. Such products are generally regarded as safe and, at typical doses, exposure to the compound of formula (G2) from their consumption is around 1 mg/day.

The anti-diabetic and anti-obesity effects of one herbal formulation has been verified in an experimental animal model, in which hyperlipidaemic Wistar rats received either a single dose equivalent to 0.6 mg compound formula (G2)/Kg or 10 daily doses up to 0.4 mg/Kg. No toxicity was reported and the results indicated the herbal formulation's ability to reduce body weight gain, and lower concentrations of plasma triglycerides, and fasting and postprandial blood glucose in animals on a high energy diet. In other studies, herbal extracts have been administered daily to rats at doses estimated to be equivalent to 5-50 mg/Kg for up to 52 weeks with no observable toxic effect.

Predictive Toxicology Screen

The compound of formula (G2) was screened for toxicity liabilities using a validated Acute Toxicity assay. Fertilized eggs were obtained from breeding pairs of adult Tuebingen (Tu) zebrafish and arrayed at the 2-4 cell stage of development into 24-well culture plates containing fresh 0.3× Danieau's solution. Plates were incubated at 28.5° C. in a humidity controlled environment prior to assessment. Stock concentrations of Compound were produced by serial dilution in 100% DMSO (final concentration exposed to larvae, 0.5%). Screening was performed at seven doses (1, 5, 25, 50, 100, 200 and 500 mM) alongside VASTox internal controls and vehicle. Dosing of Compound took place at 72 h post fertilisation (hpf; at which point embryogenesis is complete) with visual assessment of lethality and gross morphology at 96 hpf (24 h incubation). 14 larvae were exposed to each dose of Compound giving a total of 84 larvae assessed (excluding controls). At 96 hpf, larvae were observed and screened using a dissecting stereomicroscope for the presence or absence of: (1) heartbeat; (2) circulation; (3) necrosis; and (4) motility (touch response). If all four criteria were satisfied, a larva would be classified as dead. The compound was screened blind.

Results obtained at concentrations of 1 mM, 5 mM, 25 mM, 50 mM, 100 mM, 200 mM, 500 mM showed that the compound of formula (G2) did not cause acute toxicity to zebrafish larvae when exposed via an aqueous dose.

Example 9

Quality Control Process 10 g of dried herbal food additive is put into a 250 ml conical flask then enough 50% ethanol/water added to soak the plant material, allowing 2 cm extra solvent on top. This is left for 15 hours or overnight to extract. The extract is filtered using a Buchner funnel. The less polar components may be extracted for HPLC analysis for example. The plant material is either discarded or kept for sequential extraction with dichloromethane (DCM). Preferably fresh material is used for the DCM step but if insufficient is available, a sequential extraction can be performed or might be used to further characterize the components). HP20 resin may be used to clean the extracts to make them more suitable for HPLC analysis.

Dowex 50 resin (50-100 mesh) (or equivalent such as Amberlite IR120) is prepared by adding excess 2M HCl and soaking for a minimum of 15 minutes. The resin is then washed with excess deionized water to pH 7. The prepared resin is poured into 10×1 cm columns and reservoirs attached. The columns are washed with 25 ml of 50% aqueous ethanol to equilibrate the resin with the same solvent as used to prepare the plant samples. For each column, the reservoir is filled with the extract which is allowed to pass slowly through the resin.

The pH of the eluent is monitored which should be around 1 or 2. If it rises to 6 or 7 then the resin is exhausted. If this should happen, a little more resin is added to the top of the column and if necessary the whole sample is applied to the column again to ensure binding of all of the ionic components. After all of the sample has been applied to the column, it is washed with 75 ml of 50% aqueous ethanol followed by 75 ml of water. These washings are discarded normally for ISA analysis but can be analysed for unretained components such as flavonoids and sugars. The water is used to remove the alcohol and other unretained components prior to eluting the bound constituents.

The column is eluted with 100 ml of 2M ammonium hydroxide and this is collected in a 250 ml round bottom flask. This is evaporated to 3-5 ml on a rotary evaporator at less than 40° C. and transferred to a weighed 7 ml vial. The drying is completed by blowing down with nitrogen and/or freeze-drying. Care is taken to dry the samples on the same day and not to leave them sitting in the ammonia solution longer than necessary (typically less than 15 minutes) as compound degradation could otherwise occur. 1-3 mg of each dried sample is placed in GC vials and freeze dried again prior to derivatisation for analysis.

Notes (a) HP-20 Resin

Diaion HP-20 (manufactured by Sumitomo Ltd) is a styrene-divinylbenzene polymer resin. It is hydrophobic and adsorbs lipophilic compounds and weak acids. The synthetic adsorbent HP and SP series are insoluble three-dimensional crosslinked polymers with macropores. They do not possess ion exchange or other functional groups, however they have a large surface area and are able to absorb a variety of organic substances by means of van der Waals' forces. The polymer matrix can be classified as either the aromatic (styrene-divinylbenzene) type or the acrylic (methacrylic) type.

Once compounds are adsorbed they can be washed off the resin by the application of a suitable solvent. HP-20 is used in the following manner to remove excessive amounts of fats and chlorophyll from dichloromethane (DCM) extracts of plants.

The solubilised extract is dried under vacuum onto the resin. The resin is eluted with methanol containing increasing amounts of acetone (up to 30% acetone). This is enough to wash off all compounds of interest whilst leaving fats and chlorophylls adsorbed onto the HP-20 resin. The HP-20 resin is cleaned for re-use by washing with acetone and hexane. This washes off all unwanted compounds and the resin can be used once again after a final wash with methanol.

(b) Ion Exchange Chromatography

Samples are initially processed by extraction using approximately 50% aqueous alcohol, which separates the polar constituents from the more non-polar components of each plant and denatures any proteins that may be present in the extract. The extracts are then processed by ion exchange chromatography which separates and concentrates the ionic compounds in each extract (predominantly alkaloids, amino acids and small amines) from the non-ionic compounds which would also be present in the extracts (mainly sugars, fats and most of the phenolic compounds). The samples are then analysed in enzyme assays, by GC-MS or HPLC.

The filtered extracts are loaded onto Dowex 50W-X8 resin, which is a polystyrene resin cross-linked with divinylbenzene. It is a strongly acidic cation exchanger which can be used in either the free acid or hydrogen ($H^+$) form or in the salt form e.g. ammonium ($NH_4^+$) salt. Both forms of the resin adsorb cations from solution and release an equivalent number of counter-ions back into solution (either $H^+$ or $NH_4^+$ ions, depending on the form of the resin used). In the $H^+$ form, Dowex 50W-X8 resin adsorbs all ionic compounds from solution (except very strong acids), regardless of their charge, and this is the preferred form.

On adsorption of cations from the extract, protons are displaced from the resin causing the pH of the eluate to fall from pH 6.0 (the pH of the distilled water used to rinse the resin prior to use) to approximately pH 2.0, depending on the concentration of the sample. The more dilute the sample, the smaller the drop in pH. However, once the resin capacity has been reached, continued sample loading causes the pH to rise to that of the crude extract itself.

The Dowex 50W-X8 resin (50-100 mesh size) is prepared for use by washing with 2M HCl to ensure complete conversion to the $H^+$ form. The excess acid is removed by extensive rinsing with distilled water. After the crude extract has been loaded onto the resin, the column is washed with distilled water to remove any unbound material until the pH of the eluate rises to that of the water itself. The bound compounds are eluted with a 2M solution of ammonium hydroxide ($NH_4^+OH^-$). The column is washed to pH 6.0 with water and the ammonia is removed from the sample by evaporation under reduced pressure at 40° C. using a rotary evaporator.

ISAs of the invention can be further purified by binding them to anion exchange resin such as Amberlite CG400 in the hydroxide form. The ISAs can be displaced with acids such as 1M acetic acid and dried. The resin is prepared for use by soaking for 1 hour in 1M NaOH prior to washing with water to pH 8.

(c) Gas Chromatography-Mass Spectrometry (GC-MS)

Gas-liquid chromatography is a process whereby a complex mixture of volatile substances is separated into its constituents by partitioning the sample between an inert gas under pressure and a thin layer of non-volatile liquid coated on an inert support inside a heated column. In order to achieve a good separation of specific compounds in a mixture, it is crucial to use a column with the correct characteristics. The nature of the solid support, type and amount of liquid phase, method of packing, overall length and column temperature are important factors. Preferably capillary columns coated with a non-polar liquid phase (25 m×0.22 mm id×0.25 μm BPX5 stationary phase, produced by SGE Ltd.) or equivalents thereof are used.

Many compounds are unsuitable for direct injection into a gas chromatograph because of either their high polarity, low volatility or thermal instability. Compounds that are highly hydroxylated are difficult to vapourise because of inter-molecular hydrogen bonding. However, by replacing the hydroxyl hydrogens with other chemical groups, they can be made sufficiently volatile for GC analysis. The two most popular means of derivatising hydroxyl groups are acetylation and silylation, where acetylates [$CH_3CO-O-R$] or silyl ethers, e.g. trimethylsilyl (TMS) ethers [$(CH_3)_3Si-O-R$] are formed. Preferred is the silylation of samples prior to analysis using Sigma Sil A (a mixture of trimethylchlorosilane, hexamethyldisilazane and pyridine 1:3:9) produced by the Sigma Chemical Company. An alternative is Pierce Tri-Sil. Derivatisation is achieved by the addition of 100 μl of the trimethylsilylation reagent to each mg of dried material in a sealed vial (the reagent degrades in the presence of water) and the reaction is completed by heating the samples at 60° C. for 15 minutes.

The trimethylsilyl ethers in each derivatised sample are separated on the column using a temperature programme. A temperature programme is used as this allows the rapid separation of compounds of a very wide boiling range.

In electron impact mass spectrometry the effluent from the gas chromatograph, which contains the separated and vaporised compounds, is passed into the ion chamber of the mass spectrometer which is under a high vacuum. The molecules are bombarded by a beam of electrons accelerated from a filament which ionises and fragments them. Initially, one electron is removed from each molecule to form a positively charged molecular ion ($M^+$, i.e. a radical cation). Breakage of bonds relative to bond strength occurs rapidly in the molecular ion to generate fragment ions. The manner in which molecules fragment is highly characteristic and can be used as a form of 'fingerprint' identification. The various ions are accelerated into the analyser portion of the mass spectrometer where they are sorted according to their mass to charge ratios (m/z values) which are equivalent to the molecular weights of the fragments. The ion signal is amplified by an electron multiplier and the mass spectrum is plotted from low to high mass. The m/z values are plotted against relative abundance of the ions to give the visual 'fingerprint'.

(d) HPLC-PDA/MS/ELS (Evaporative Light Scattering Detection)

With this technique, samples are dissolved in a suitable solvent and separated on a column using a solvent mixture that is pumped under pressure through the column. Three detectors are used; a mass spectrometer, as described above, and a photodiode array system that measures whether the compounds absorb light at wavelengths in both the UV and visible ranges and a light scattering detector (ELS). The ELS is particularly well suited to detect the imino sugar acids and imino sugars that usually lack a chromophore.

A Waters Integrity™ HPLC-PDA/MS system fitted with a reverse phase 08 HPLC column (50 mm×2.1 mm id×3.5 µm, Waters) was used to analyse non-polar compounds extracted by DCM and cleaned using HP20 resin. The rate of solvent flow through the column was 0.35 ml/min and a linear gradient starting at 90% water and 10% acetonitrile (containing 0.01% trifluoroacetic acid) was used, rising to 100% acetonitrile over 6 minutes and held for a further 6.5 minutes.

Absorbance (photodiode array—PDA) data was collected from 200-600 nm and mass spectral data collected between 71 and 600 m/z. Imino sugar acids are not well resolved or detected by such HPLC systems but many other groups of phytochemicals are that may co-occur with imino sugar acids in herbal preparations. ELS detection allows the imino sugars and imino sugar acids to be observed. However, other forms of HPLC are available that are better suited to detection of carbohydrates and imino sugars and imino sugar acids; examples are the Dionex carbohydrate HPLC systems and HILIC (hydrophilic interaction chromatography) coupled for example to electrochemical detectors, mass spectrometers or ELS detectors.

An example of a HILIC system suited to imino sugars and imino sugar acids is an HPLC fitted with a SeQuant HPLC column (ZIC-HILIC packing, 150×4.6 mm, 3.5 um particle size, 200 A pore size) with a mobile phase of 40:55:5 of Water:Acetonitrile:100 mM Ammonium Acetate pH5.7 and a flow rate of 0.5 ml/min. Detection using a Polymer Laboratories PL-ELS 1000 (light scattering detector) gave good resolution of imino sugars and imino sugar acids.

Table Showing Examples of Separation of Amino Acids, Imino Sugars and Imino Sugar Acids Using a HILIC HPLC System

| Compound Name | Retention Time in Minutes |
| --- | --- |
| Aspartic Acid | 3.53 |
| Adenine | 4.00 |
| Phenylalanine | 4.20 |
| Tyrosine | 4.72 |
| Valine | 4.88 |
| Imino sugar acid S9 | 4.97 |
| Proline | 5.20 |
| Imino sugar acid G2 | 5.27 |
| Alanine | 5.37 |
| Asparagine | 5.59 |
| 6-epi-castanospermine | 6.49 |
| Castanospermine | 6.55 |
| DNJ | 11.23 |
| Casuarine | 11.61 |
| Swainsonine | 14.33 |

-continued

| Compound Name | Retention Time in Minutes |
| --- | --- |
| DMDP | 14.64 |
| 3,7-diepicasuarine | 14.81 |
| Australine | 16.26 |
| DAB | 17.19 |

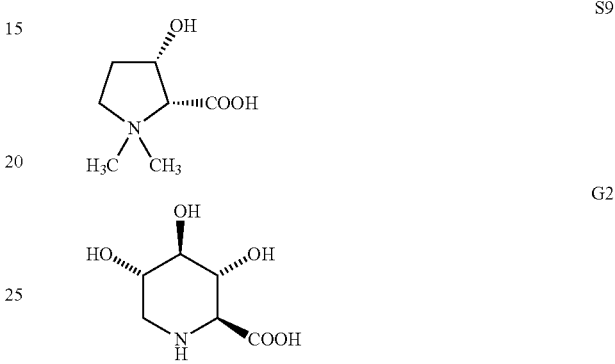

A Dionex HPLC system used for separating and detecting imino sugars and imino sugar acids consisted of a Dionex ION PAC CS10 4×250 mm column with an ION PAC CG10 4×50 mm guard column and a mobile phase of Methane Sulphonic Acid diluted to 80 mM and water. The pump was a Dionex P680, to deliver eluent A (80 mM MSA) and eluent B (WATER, ultrapure) as required, at a total flow rate of 1 ml/min. The injector was a Rheodyne manual injector and the oven, a Dionex LC30, was used to maintain column and guard at 30C. A pneumatic controller (Dionex PC10, (He gas, ~1.5 ml/min NaOH at 60 psi) was used to add 300 mM NaOH to the eluent flow between the column and the detector. The detector was a Dionex ED40 Electrochemical Detector and the data analysed using Dionex Chromeleon software.

Example 10

Lack of Inhibition of Digestive Glucosidases by Compound G2

Deoxynojirimycin (DNJ), N-butyl-DNJ (Zavesca®) and the N-hydroxymethyl-derivative (Miglitol, Glyset®) developed by Bayer for treatment of Diabetes type 2 are potent inhibitors of glucosidases (see Watson et al., 2001, Phytochemistry 56: 265-295). The inhibition of glucosidases is responsible both for gastrointestinal disturbance (side effects of the drugs) and the benefits to diabetic patients of taking Glyset® which functions through slowing of glucose release and uptake in the GI tract, thus controlling post-prandial blood glucose levels. The iminosugar acids of the invention such as G2 have the advantage of being able to control blood glucose levels through a mechanism not involving inhibition of digestive glucosidases and, therefore, avoid the side effects of DNJ and drugs derived from it.

Inhibitory Effect of G2 and DNJ on Rat Intestinal Glycosidases

|  | G2 | $IC_{50}$ value µM DNJ* |
|---|---|---|
| maltase | LI | 0.36 |
| isomaltase | NI | 0.3 |
| sucrase | NI | 0.21 |
| cellobiase | NI | ND |
| lactase | NI | ND |
| trehalase | NI | ND |

ND = not determined;
*from Yasuda et al., 2002, J. Nat. Prod. 65, 198-202.
LI = inhibition not reaching 50% at 1 mM;
NI = no inhibition at 1 mM
Enzyme activities were prepared from brush border membranes of rat small intestine using disaccharides as substrates as described by Yasuda et al. 2002.

Acarbose, another glucosidase inhibitor used for diabetes type 2 which reduces glucose release and uptake, is also reported to be a potent inhibitor of rat small intestine maltase ($IC_{50}$ 0.16 µM) and sucrase ($IC_{50}$ 2.9 µM) (Kato et al., 2008, J. Agric. Food Chem. 56, 8206-8211).

A comparison of the activity on rabbit digestive disaccharidases of compounds of the invention G2, S2, T1 and T2 and DNJ and Zavesca have also been made. The results of this comparison are shown in the table below. G2, S2 and T2 showed no inhibition of the disaccharidases at 0.8 mM whereas T1 showed very weak inhibition of maltase and sucrase in comparison to DNJ and Zavesca. Isomaltase inhibition was not determined for S2 and T1.

Inhibitory Effect of Compounds of the Invention and DNJ and Zavesca on Rabbit Intestinal Glycosidases

|  | sucrase IC50 (uM) | maltase IC50 (uM) | isomaltase IC50 (uM) |
|---|---|---|---|
| Zavesca | 0.22 | 0.97 | 0.19 |
| DNJ | 0.09 | 0.18 | 0.02 |
| G2 | NI | NI | NI |
| S2 | NI | NI | ND |
| T1 | 6.1 | 19 | ND |
| T2 | NI | NI | NI |

Rabbit Disaccharidase Inhibition Assay Method

Sucrose (8.3 mM), maltose (5 mM) and isomaltose (6.3 mM) substrates were made using 0.2 M MacIlvaine (citrate-phosphate) buffer, pH 6.0. The glucose detection reagent was prepared according to the supplier's instructions (Megazyme Ltd). Linearity of the timecourse of the reaction between the glucose detection reagent and glucose was tested using a series of glucose dilutions.

Mammalian Disaccharidase Preparation

The method for preparation of mammalian small intestine mucosal disaccharidases was based on Griffiths (1998), omitting ammonium sulphate fractionation steps. The small intestine was dissected out of a female wild rabbit, and opened longitudinally using a scalpel. The mucosal layer was scraped off using the edge of a clean microscope slide, and placed into 3 ml of $dH_2O$. The mucosal layer suspension was centrifuged at around 1000 rpm for 30 seconds to sediment tissue debris. The supernatant (6 ml) was removed, and centrifuged again at 3500 rcf for 1 minute to remove fine particulates from suspension. The supernatant was diluted to give 0.2-0.25 mg/ml protein and stored at −30° C.

Enzyme assays were carried out using 5-15 µl of enzyme preparation, 5 µl of test compound (or $dH_2O$ for controls) and 15-25 µl of substrate solution. Reactions were covered using a sheet of plate sealing film, and incubated at 37° C. for 60 minutes. Glucose (from disaccharide hydrolysis) was quantified by adding 200 µl of glucose detection reagent and incubating the reactions for a further twenty-five minutes. Absorbance was measured at 510 nm against control blanks.

In this way enzyme inhibition of mammalian small intestine mucosal sucrase, maltase and isomaltase could be determined.

Example 11

Correlation of the Presence of Iminosuqar Acids in Plants Claimed to have Anti-Diabetic Activity The imino sugar acids are rare in plants but they have also been identified in *Lotus* species (Fabaceae), Pumpkin (*Cucurbita* species), *Aspalanthus linearis* (Rooibos), *Alexa* species and *Castanospermum australe* (Fabaceae), *Eugenia* and *Syzygium* species (Myrtaceae), *Lycium barbarum* (Goji, Solanaceae) and *Andrographis paniculata* (Acanthaceae).

*Gymnema sylvestre* is a plant claimed to have anti-diabetic or anti-obesity activity and has clinical evidence of activity (e.g. see Baskaran et al., 1990, Antidiabetic effect of a leaf extract from *Gymnema sylvestre* in non-insulin-dependent diabetes mellitus patients. J Ethnopharmacol. 30:295-300 and Shanmugasundaram et al., 1990, Use of *Gymnema sylvestre* leaf extract in the control of blood glucose in insulin-dependent diabetes mellitus J Ethnopharmacol. 30:281-94). The present inventors have now discovered that *Gymnema sylvestre* leaves, seeds and stems contain the iminosugar acid G2. Products sold commercially for weight loss such as Floressance "*Citrus, Garcinia, Gymnema* concentre" capsules also contain G2 (2.4 mg per capsule in Lot 8205CC). The presence of G2 or other iminosugar acids in *Gymnema* has not been reported by any other researchers. To date published research has concentrated on other components of *Gymnema* that affect sweet taste such as Gymnemic acids, which unlike G2 are not shown to be orally available.

We have also discovered that the plant Gurana (also called Guarana) *Paullinia cupana* contains an N-methyl-3-deoxy-form of G2 also reported as Glabrin from *Pongamia glabra* (this structure had no stereochemistry reported). Gurana has claims for weight loss, e.g. see Anderson T and Foght J, 2001, Weight loss and delayed gastric emptying following a South American herbal preparation in overweight patients. J. Hum. Nutr. Diet 14, 243. Although Gurana is well known to contain caffeine which is claimed to give some protection from development of diabetes type 2, iminosugar acids related to compound G2 are key components of Gurana with anti-diabetic and anti-obesity activity. *Pongamia* is orally toxic due to other components.

The present inventors have also isolated iminosugar acids of the pyrrolidine structure from other plant species claimed to have anti-diabetic activity such as Bitter Orange which contains various stachydrines as examples shown below.

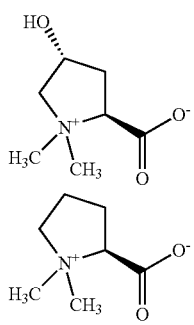

The present inventors have also recently isolated from *Citrus* a compound identified as an acid of a pyrrolizidine alkaloid and related to epialexaflorine (see Watson et al., 2001) shown below. It also contains compounds which are N- and O-butyl-derivatives of G2 and O-butyl-N-acid-derivatives of Deoxynojirimycin-like compounds (e.g. T3) proven by semi-synthesis and GC-MS analysis of the compounds and the *Citrus* extracts as trimethylsilyl-derivatives.

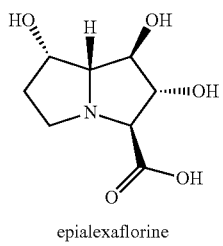

epialexaflorine

Chinese pumpkin (or Siam Pumpkin) is claimed to increase beta cells in diabetic rats, Xia, T., 2007, Journal of the Science and Food and Agriculture 87, 1753-1757. The present inventors have shown that open chain iminosugar acid compounds (e.g. example P3) are present in seeds and fruit of the European pumpkin (*Cucurbita pepo*). Several Cucurbitaceae species have claims for anti-diabetic activity including Bitter melon (*Momordica charantia*) which shows several potential iminosugar acids in the CG400 OH-bound fraction analysed by GC-MS and by characteristic activity in glucuronidase and hexosaminidase assays.

The therapeutic association of iminosugar acids and diabetes or weight control is also shown by the example of *Stevia rebaudiana* which has been shown to control blood glucose levels and to modulate insulin levels. While research effort by others has focused on steviosides and rebaudiosides and related glycosides these appear to have no pharmacological activity, e.g. see Barriocanal L A et al., 2008, Apparent lack of pharmacological effect of steviol glycosides used as sweeteners in humans. Regul. Toxicol. Pharmacol. 51:37-41. The plant, however, has proven anti-glycaemic activity and was used traditionally to treat diabetes in South America, e.g. see Ferreira E B et al., 2006, Comparative effects of *Stevia rebaudiana* leaves and stevioside on glycaemia and hepatic gluconeogenesis. Planta Med. 72:691. The discovery of iminosugar acids such as S2 in *Stevia* therefore suggests that removal of these compounds eliminates the anti-diabetic activity of *Stevia*.

Example 12

Measurement of Glycosidase Activities of Iminosugar Acids in Plant Claimed to have Anti-Diabetic or Anti-Obesity Activity Iminosugar acids can show distinctive inhibition of glucuronidase and/or hexosaminidase activities which are not shown by other iminosugars such as deoxynojirimycin (DNJ), Miglitol and DAB (1,4-dideoxy-1,4-imino-D-arabinitol); these iminosugar compounds appear to exhibit potential therapeutic activity in diabetes or obesity through inhibition of glucosidases and glycogen phosphorylase but therefore also have side effects caused by inhibition of digestive disaccharidase activity.

Compound G2 of the invention has an $IC_{50}$ against mammalian glucuronidase of 107 µM while the N-hydroxyethyl-derivative of G2 is more potent against the glucuronidase ($IC_{50}$ 60 µM) and mammalian β-N-acetylglucosaminidase ($IC_{50}$ 12.2 µM). DNJ is not inhibitory to either enzyme activity at 0.8 mM but N-propionoic DNJ is inhibitory to both glucuronidase ($IC_{50}$ 50 µM) and the hexosaminidase ($IC_{50}$ 32 µM).

Table Showing Comparison of the Glycosidase Inhibition Profile of the Iminosugars DNJ and Miglitol with Three Iminosugar Acids of the Invention (Inhibition Shown as % Inhibition at 0.8 mM—$IC_{50}$ Values in Italics)

| Assay | DNJ | Miglitol | G2 | S2 | T3 |
|---|---|---|---|---|---|
| α-D-glucosidase (Yeast) | 36 | NI | NI | NI | NI |
| α-D-glucosidase (*Bacillus*) | 100 | 83 | 49 | *51.7 uM* | NI |
| α-D-glucosidase (Rice) | 100 | 100 | 55 | NI | *259 uM* |
| β-D-glucosidase (Almond) | 64 | 99 | NI | 55 | NI |
| α-D-galactosidase Green coffee bean | NI | 19 | NI | NI | NI |
| β-D-galactosidase Bovine liver | NI | 87 | NI | 60 | NI |
| α-L-fucosidase Bovine kidney | 6 | −5 | NI | NI | NI |
| α-D-mannosidase Jack bean | 27 | 7 | 29 | NI | NI |
| β-D-mannosidase *Cellulomonas fimi* | −19 | NI | NI | NI | NI |
| Naringinase *Penicillium decumbens* | 21 | 26 | NI | NI | NI |
| N-acetyl-β-D-glucosaminidase (Bovine kidney) | NI | NI | NI | NI | *12.2 uM* |
| N-acetyl-β-D-glucosaminidase (Jack bean) | NI | NI | 10 | NI | NI |
| N-acetyl-β-D-glucosaminidase (*A. oryzae*) | NI | NI | NI | NI | NI |
| Amyloglucosidase *Aspergillus niger* | 32 | 78 | NI | NI | NI |
| β-Glucuronidase Bovine liver | NI | NI | *107 uM* | *507 uM* | *60 uM* |

Inhibition at 0.8 mM - $IC_{50}$ values in italics)
N.B. Inhibition of 50% or below at 0.8 mM indicates very weak inhibition.

Several plants claimed to have anti-diabetic activity were assessed for the ability to inhibit mammalian glucuronidase or hexosaminidase activity. Plants contain many aromatic components such as flavonoids and polyphenols that can have non-specific protein binding activity or have strong colours making the use of standard colorimetric glycosidase assays impossible. The aqueous ethanol extracts of plants were therefore fractionated using a combination of cation and anion exchange methods to purify the iminosugar acid components. The methods are familiar to those experienced in the art and involve binding the amino acids and alkaloids to a strongly acidic cation exchange resin (e.g. IR120 in the $H^+$ form), washing with water, displacing the bound components with 2M ammonia solution, concentrating under reduced pressure to remove the ammonia and then binding the iminosugar acids to a strongly basic anion exchange resin (e.g. Amberlite CG400 in the $OH^-$ form) and after washing with water, displacing the iminosugar acids with 1M acetic acid. After removal of excess acetate these fractions are suitable for glycosidase assays.

Glycosidase Assay Methods

All enzymes and para-nitrophenyl substrates were purchased from Sigma, with the exception of beta-mannosidase which came from Megazyme. Enzymes were assayed at 27° C. in 0.1 M citric acid/0.2M disodium hydrogen phosphate buffers at the optimum pH for the enzyme. The incubation mixture consisted of 10 μl enzyme solution, 10 μl of 1 mg/ml aqueous solution of extract and 50 μl of the appropriate 5 mM para-nitrophenyl substrate made up in buffer at the optimum pH for the enzyme. The reactions were stopped by addition of 70 μl 0.4M glycine (pH 10.4) during the exponential phase of the reaction, which had been determined at the beginning using uninhibited assays in which water replaced inhibitor. Final absorbances were read at 405 nm using a Versamax microplate reader (Molecular Devices). Assays were carried out in triplicate, and the values given are means of the three replicates per assay. (See Watson, A. A., Nash, R. J., Wormald, M. R., Harvey, D. J., Dealler, S., Lees, E., Asano, N., Kizu, H., Kato, A., Griffiths, R. C., Cairns, A. J. and Fleet, G. W. J. (1997). Glycosidase-inhibiting pyrrolidine alkaloids from *Hyacinthoides non-scripta*. Phytochemistry 46 (2): 255-259.)

The table below gives details of the enzymes used and the conditions of the individual assays.

| Enzyme | Source | Substrate (5 mM) | pH | [Enzyme] working stock (U/ml) | Reaction conditions (mins) |
| --- | --- | --- | --- | --- | --- |
| α-D-glucosidase | *Saccharomyces cerevisiae* | PNP-α-D-glucopyranoside | 6.8 | 0.5 | 15 |
| α-D-glucosidase | *Bacillus sterothermophilus* | PNP-α-D-glucopyranoside | 6.8 | 0.25 | 15 |
| α-D-glucosidase | Rice | PNP-α-D-glucopyranoside | 4.0 | 7.5 | 20 |
| β-D-glucosidase | Almond | PNP-β-D-glucopyranoside | 5.0 | 0.125 | 15 |
| α-D-galactosidase | Green coffee bean | PNP-α-D-galactopyranoside | 6.5 | 0.2 | 15 |
| β-D-galactosidase | Bovine liver | PNP-β-D-galactopyranoside | 7.3 | 0.1 | 15 |
| α-L-fucosidase | Bovine kidney | PNP-α-L-fucopyranoside | 5.5 | 0.4 | 15 |
| α-D-mannosidase | Jack bean | PNP-α-D-mannopyranoside | 4.5 | 0.4 | 10 |
| β-D-mannosidase | *Cellullomonas fimi* | PNP-β-D-mannopyranoside | 6.5 | 1 | 15 |
| Naringinase | *Penicillium decumbens* | PNP-α-L-rhamnopyranoside | 4.0 | 0.05 | 15 |
| N-acetyl-β-D-glucosaminidase | Bovine kidney | PNP-N-acetyl-β-D-glucosaminide | 4.25 | 0.35 | 15 |
| N-acetyl-β-D-glucosaminidase | Jack bean | PNP-N-acetyl-β-D-glucosaminide | 5.0 | 0.25 | 20 |
| N-acetyl-β-D-hexosaminidase | *Aspergillus oryzae* | PNP-N-acetyl-β-D-glucosaminide | 5.0 | 0.125 | 15 |
| Amyloglucosidase | *Aspergillus niger* | PNP-α-D-glucopyranoside | 4.5 | 20 | 30@32 |
| β-D-glucuronidase | Bovine liver | PNP-β-D-glucuronide | 5.0 | 3000 | 20 |

Results

The anion exchange resin (CG400 Oft) bound fractions of the plants *Stevia rebaudiana* and *Gymnema sylvestre* give complete inhibition of glucuronidase activity at 1.43 mg/ml. This inhibition is probably due to the high concentration of compound G2 in *Gymnema* and compounds such as S2 in *Stevia*.

Examples of other plants studied with claims for anti-diabetic and or anti-obesity activity are Goji fruits (*Lycium barbarum*), *Theobroma cacao* nibs, *Aspalanthus linearis* (Rooibos tea), *Hoodia gordonii*, Korean Ginseng (*Panax ginseng*) and Soya bean (*Glycine max*). These were all fractionated into CG400 OH– bound fractions prior to assays. The results in the two tables below are expressed as % inhibition by 1.43 mg/ml except for caffeine which was run at 143 ug/ml as a control compound for Cacao nibs.

Mean % Inhibition Shown by Iminosugar Acid
Fraction of Cacao Nibs and Caffeine

| Enzyme | Source | Caffeine 143 ug/ml | Cacao nibs DT0181/121/2 |
|---|---|---|---|
| N-acetyl-β-D-glucosaminidase | Bovine kidney | 1.3 | 19.6 |
| β-glucuronidase | Bovine liver | −2.4 | 30.5 |

Mean % Inhibition Shown by Iminosugar Acid
Fractions of Plants Claimed to have Anti-Diabetic
or Weight Control Properties

| Enzyme | Source | Hoodia tablets DT0181/143/1 | Korean ginseng AM0241/119/2 | Korean ginseng DT XCD01 | Goji | Rooibos | Soya beans |
|---|---|---|---|---|---|---|---|
| N-acetyl-β-D-glucosaminidase | Bovine kidney | 73.8 | −16.1 | 7.8 | 25 | 5 | 88 |
| β-glucuronidase | Bovine liver | 41.2 | 72.9 | 36 | 3 | 27 | 87 |

It can be seen from the results obtained with the plants above that they show some inhibition of either bovine glucuronidase or hexosaminidase. The GC-MS analysis of the CG400 OH− (anion exchange resin) bound fractions showed that levels of possible iminosugar acids in these samples were not as high as in *Stevia* or *Gymnema* and there were many other major components such as protein amino acids which will have diluted the inhibitors in such complex mixtures. However, soya beans for example show surprisingly strong inhibition of both enzyme activities. Rooibos and Goji berries show a relatively low level of inhibition of the enzymes but both show an activity. Korean *Ginseng* shows a strong inhibition of the glucuronidase activity in two different samples tested, while *Hoodia* gives inhibition of both enzyme activities. Further purification and isolation work is needed to fully characterize the components in these iminosugar acid fractions giving the inhibitions. Once purified the strength of the inhibition should increase greatly.

Example 13

In Vivo Activity of Compound G2—Enhancement
of Insulin Levels in Ddy Mice

Method 7 week old ddy mice (weight 30-31 g) were divided into 4 groups (groups 1 to 4). Each group had 3-4 mice. All test mouse were fasted for 16 hours before being given the test compounds.

The aim of this experiment was to determine if G2 (here coded BR1) can stimulate insulin release.
Group 1: Control. un-treated mice (without glucose and G2).
Group 2: Oral administration of glucose alone.
Group 3: Oral administration of G2 alone.
Group 4: Oral administration of G2 with glucose.

Figure 2:
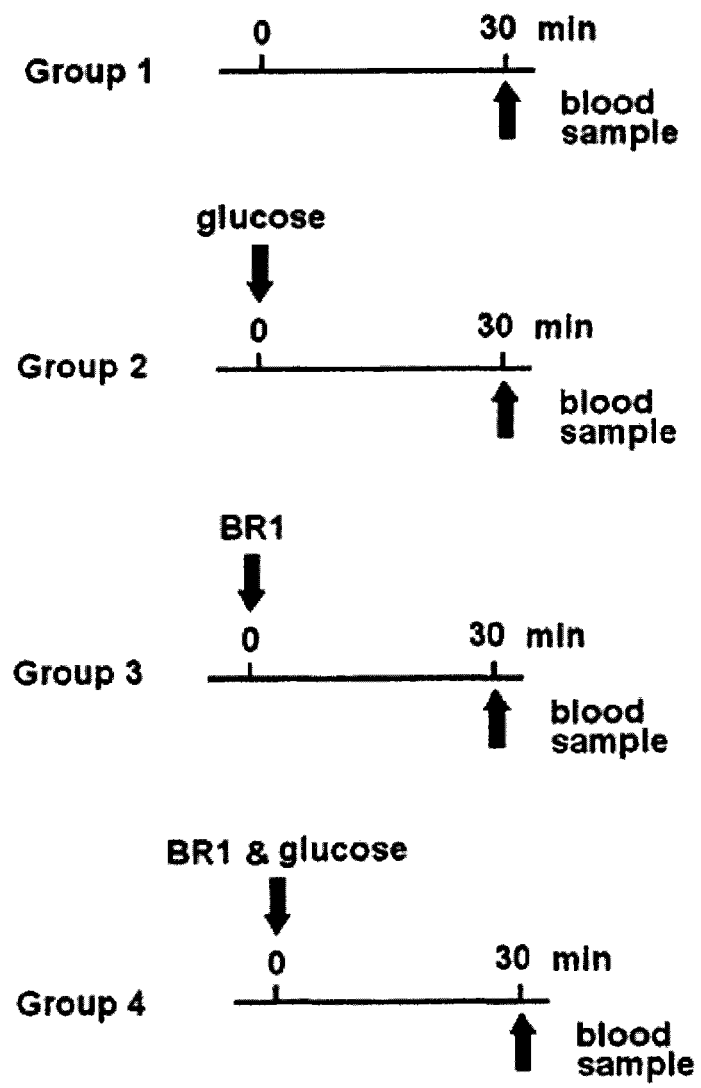
FIG. 2 shows a graphic of a test performed to determine serum insulin levels of mice.

Serum insulin levels were measured after 30 minutes (see FIG. 2).

Results

Comparing Groups 1 (un-treated) and Group 3 (oral administration of G2 alone) it is clear that G2 did not affect the insulin level. However, combination of glucose and G2 is much effective than glucose alone. These results suggest that G2 does not affect insulin release itself but it appears to enhance levels.

Figure 3:
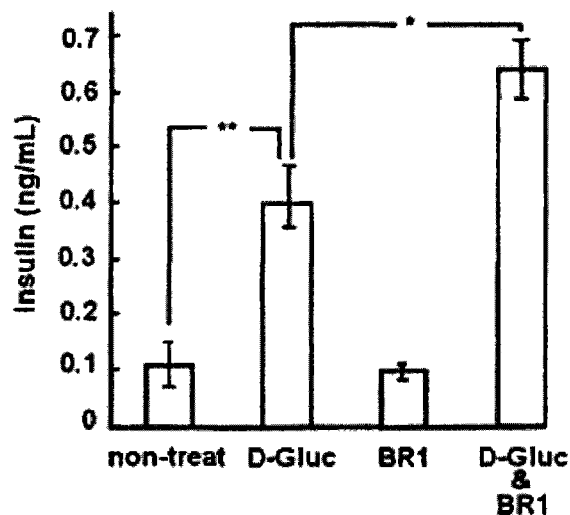
FIG. 3 shows a comparison of serum insulin levels of mice untreated and treated with an embodiment of the invention.

FIG. 3 Effects of G2 (BR1) (100 mg/kg Body Weight) on Serum Insulin Levels.

Serum insulin concentrations of male ddy mouse after 30 minutes later an oral load with or without D-glucose (2.5 g/kg body weight). Each value represents the mean±SEM (n=3-4). * $P<0.05$, ** $P<0.01$.

Example 14

In Vivo Activity of Compound G2—Control of
Blood Glucose Levels in Ddy Mice

Method 7 weeks old ddy mice (weight 30-31 g) were divided into 4 groups (from group 1 to 4). Each group had 5 mouse. All test mouse were fasted for 16 hours for this experiment.

The aim of this experiment was to show if G2 (here coded as BR1) could suppress a hyperglycemia after a meal. Thus, maltose was chosen as the loading sugar as used for Bayer's glucosidase inhibitor Glucobay. Either maltose (2.5 g/kg) or Surose (2.5 g/kg) or starch (1.0 g/kg) can be used but maltose is most popular.

The hypothesis was that if G2 can suppress the blood glucose level it may:

1) inhibit maltase (inhibit to change from maltose to glucose).

2) inhibit glucose transport.

3) stimulate insulin release.

4) inhibit glycogenphosphorylase.

5) another activity

Figure 4:
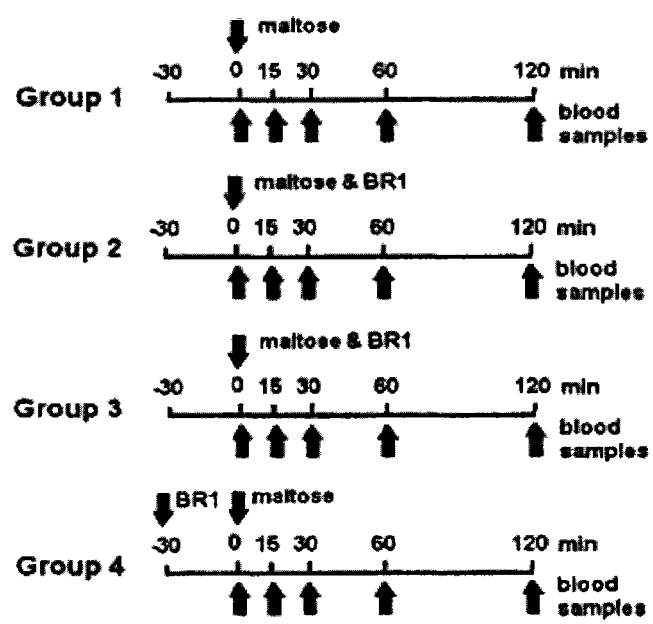
FIG. 4 shows a graphic of a test performed to determine the effects of an embodiment of the invention in mice.

Thus, there were 4 groups (see FIG. 4).

Group 1: Control. Maltose-loading only (without G2 condition).

Group 2: oral administration of G2 with maltose (same time).

Group 3: intraperitoneal injection of G2 and oral administration of maltose (same time).

Group 4: oral administration of G2 30 minutes before maltose-loading. (Glucobay is taken 30 minutes before meals).

Results

It was shown that G2 can suppress hyperglycemia in every group. Curve of group 2 (p.o.) and group 3 (i.p.) is almost same. This result is very important because if inhibition mechanism of G2 is "inhibition of maltase" and/or "inhibition of glucose transporter", the i.p. route would not inhibit hyperglycemia. Thus, the site of action of G2 is not in the intestinal tract and maybe the pancreas. Furthermore, this result showed that G2 is absorbed into the blood very quickly.

Figure 5A:
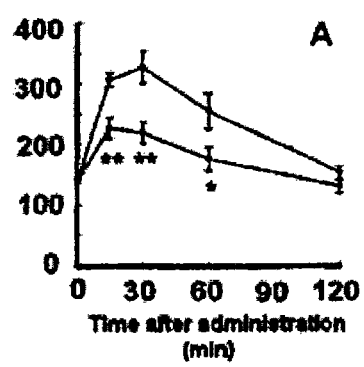
FIGS. 5A, 5B, and 5C show a comparison of blood glucose levels of mice treated with an embodiment of the invention under different conditions.
Figure 5B:
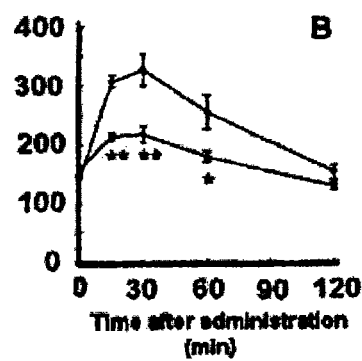
Figure 5C:
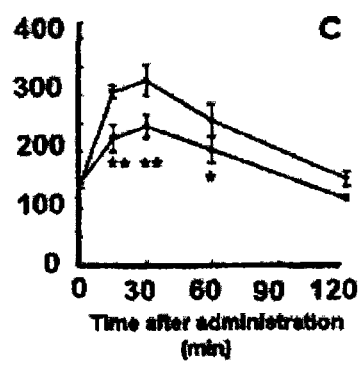

See FIG. 5 for the effects of G2 (BR1) on blood glucose levels.

Example 15

Inhibition of Mammalian β-Glucuronidase and β-N-Acetylglucosaminidase by Iminosugar Acids The following tables show comparative % inhibitions of commercially available (Sigma) bovine β-glucuronidase (liver) and β-N-acetylglucosaminidase (kidney) by iminosugar acids and amino acids at approximately 0.8 mM. Where strong inhibition was observed $IC_{50}$ values were calculated and are shown as μM next to the % inhibition values. It can be seen that the ability to inhibit the glucuronidase and hexosaminidase activities is not found in many compounds of this group other than iminosugar acids. The assays were conducted using p-nitrophenyl-substrates as described previously.

| Structure | % Glucuronidase inhibition at 0.8 nM Bovine Liver | % Nacetyl glucosaminidase inhibition at 0.8 nM Bovine kidney |
|---|---|---|
| (cyclobutane COOH/NH₂/OH structure) | −2.2 | 7.1 |
| (pyrrolizidine triol carboxylic acid) | −2.3 | 5.1 |
| (piperidine-glycoside with butanoic acid N-substituent) | 3.9 | 49.4 |
| (N-methyl-4-hydroxyproline) | −3.7 | −4.7 |
| (N,N-dimethyl-3-hydroxyproline betaine) | −4.4 | −0.6 |
| (iminosugar piperidine carboxylic acid, trihydroxy) | 88.9<br>107 uM | 2.4 |

-continued
| Structure | % Glucuronidase inhibition at 0.8 nM Bovine Liver | % Nacetyl glucosaminidase inhibition at 0.8 nM Bovine kidney |
|---|---|---|
| 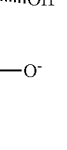 | 3.8 | 8 |
| 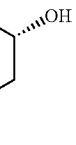 | 58.6<br>531 uM | 4.8 |
| 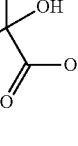 | −3.2 | −4.2 |
| 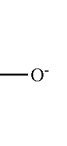 | −1.7 | 2.3 |
| 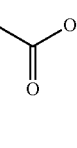 | −1.6 | 0.8 |
| 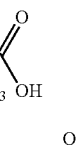 | 1.4 | 2.9 |
| 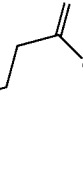 | −2 | 17 |
| 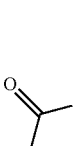 | 85.3<br>81 uM | 90.1<br>5.1 uM |

-continued

| Structure | % Glucuronidase inhibition at 0.8 nM Bovine Liver | % Nacetyl glucosaminidase inhibition at 0.8 nM Bovine kidney |
|---|---|---|
| (pyrrolidine with N-(CH2)4-COO−, CH2O−, and two OH/O− groups) | 0.8 | 8 |
| (pyrrolidine with methyl, carboxylate, and two O− groups) | 0.6 | 7.6 |
| (pyrrolidine with HO, OH, and CO2H substituents) | 13.8 | 6.6 |
| (piperidine with CH2OH, OH, OH, OH, and CO2H/NH) | 3.3 | 25.8 |
| (pyrrolidine with HOCH2-CH(OH)-, N-CH2COOH, HO, OH) | 4 | 82.3<br>137 uM |
| (piperidine with NHAc, OH, OH, CO2H) | 97.9<br>7.3 uM | 57.9 |
| (piperidinone with CO2H, HO, OH, OH) | 99.6<br>0.04 uM | −5.2 |

Examples 16 to 21

Synthesis of Imino Sugar Acids

General Alkylation Procedure

Alkyl halide (0.46 mmol) and $K_2CO_3$ (0.61 mmol) were added to a solution of iminosugar (0.31 mmol) in DMF (2 mL) and the resulting reaction mixture was stirred at 60° C. for 16 h. The solvent was removed under reduced pressure and the residue purified by ion exchange chromatography using a combination of Dowex-50WX8-400 and SPE cartridges such as POH or isolute SCX-2.

The following compounds were prepared using the general alkylation procedure:

2-((2R,3R,4R,5S)-3,4,5-Trihydroxy-2-(hydroxymethyl)piperidin-1-yl)acetic acid (G6)

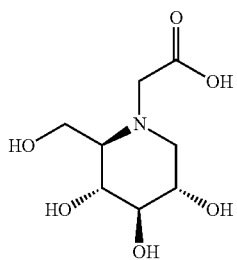 [SMILES: O=C(O)CN1C[C@H](O)[C@@H](O)[C@H](O)[C@H]1CO]

$^1$H-NMR ($D_2O$): 3.78 (1H, dd, J 2.7 Hz, J 13.2 Hz). 3.72 (1H, dd, J 2.4 Hz, J 13.2 Hz), 3.59-3.51 (1H, m), 3.41 (1H, t, J 9.5 Hz), 3.33 (2H, s), 3.23 (1H, t, J 9.3 Hz), 3.05 (1H, dd, J 5.0 Hz, J 11.6 Hz), 2.70-2.58 (2H, m); $^{13}$C-NMR ($D_2O$): 176.6, 77.8, 69.0, 68.2, 65.6, 56.8, 56.7, 56.4; MS (M+H$^+$): 222.3

2-((2R,3R,4R,5S)-3,4,5-Trihydroxy-2-(hydroxymethyl)piperidin-1-yl)propanoic acid (T1)

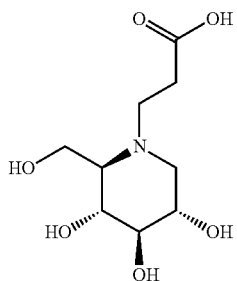 [SMILES: O=C(O)CCN1C[C@H](O)[C@@H](O)[C@H](O)[C@H]1CO]

$^1$H-NMR ($D_2O$): 3.92 (2H, s), 3.63-3.59 (1H, m), 3.49 (1H, t, J 5.9 Hz), 3.35-3.29 (3H, m), 3.12 (1H, m), 2.79 (1H, m), 2.70 (1H, m), 2.49-2.46 (2H, m); $^{13}$C-NMR ($D_2O$): 76.6, 68.1, 67.0, 65.3, 54.9, 53.6, 49.2, 31.0; MS (M+H$^+$): 236.0

(2S,3R,4R,5S)-Butyl 1-butyl-3,4,5-trihydroxypiperidine-2-carboxylate (T2)

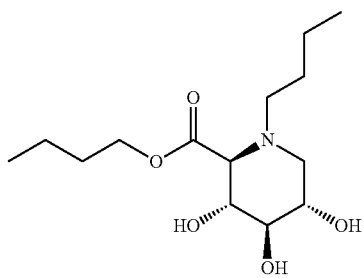 [SMILES: CCCCOC(=O)[C@@H]1[C@@H](O)[C@H](O)[C@@H](O)CN1CCCC]

$^1$H-NMR ($D_2O$): 4.20-4.07 (2H, m), 3.54-3.48 (1H, m), 3.47 (1H, t, J 5.8 Hz), 3.19 (1H, t, J 5.6 Hz), 3.04 (1H, dd, J 2.9 Hz, J 6.9 Hz), 2.91 (1H, d, J 5.9 Hz), 2.39 (1H, dt, J 3.2 Hz, J 6.8 Hz), 2.25 (1H, m), 2.07 (1H, t, J 6.6 Hz), 1.57 (2H, m), 1.43 (1H, m), 1.30 (3H, m), 1.15 (2H, m), 0.81 (3H, t, J 4.5 Hz), 0.77 (3H, J 4.4 Hz); $^{13}$C-NMR ($D_2O$): 77.1, 72.2, 71.2, 68.8, 66.2 (2×), 54.8, 29.8, 26.4, 19.9, 18.5, 13.0 (2×); MS (M+H$^+$): 290.3

(2S,3R,4R,5S)-3,4,5-Trihydroxy-1-(2-hydroxyethyl)piperidine-2-carboxylic acid (T3)

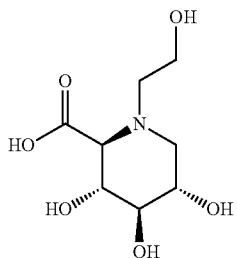 [SMILES: O=C(O)[C@@H]1[C@@H](O)[C@H](O)[C@@H](O)CN1CCO]

$^1$H-NMR ($D_2O$): 3.80-3.67 (3H, m), 3.55 (1H, t, J 5.8 Hz), 3.40 (1H, m), 3.32 (1H, t, J 5.6 Hz), 3.10 (1H, m), 3.03 (1H, m), 2.84 (1H, m), 2.59 (1H, m); MS (M+H$^+$): 222.5

2-((2R,3R,4R,5R)-3,4-Dihydroxy-2,5-bis(hydroxymethyl)pyrrolidin-1-yl)acetic acid (S2)

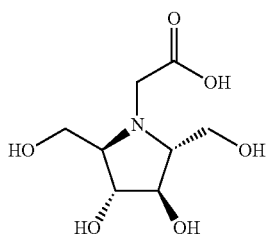 [SMILES: O=C(O)CN1[C@H](CO)[C@@H](O)[C@H](O)[C@H]1CO]

$^1$H-NMR ($D_2O$): 4.13 (2H, dd, J 0.9 Hz, J 3.2 Hz), 3.95 (1H, d, J 9.8 Hz), 3.91 (5H, m), 3.66 (2H, bs). $^{13}$C-NMR ($D_2O$): 74.2 (2×), 69.8 (2×), 56.6 (2×), 52.1; MS (M+H$^+$): 222.3.

2-((2R,3R,4R)-3,4-Dihydroxy-2-(hydroxymethyl)
pyrrolidin-1-yl)acetic acid (T4)

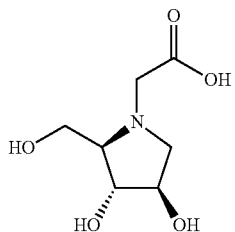 [SMILES: O=C(O)CN1C[C@@H](O)[C@H](O)[C@H]1CO]

$^1$H-NMR (D$_2$O): 4.27 (1H, m), 4.05 (1H, m), 3.69 (1H, d, J 9.8 Hz), 3.91 (2H, m), 3.76 (1H, d, J 9.8 Hz), 3.72 (1H, m), 3.55-3.52 (2H, m). $^{13}$C-NMR (D$_2$O): 76.0, 73.6 (×2), 59.7, 57.8, 57.6; MS (M+H$^+$): 192.3.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:
1. A method of treating type 2 diabetes in a human patient while reducing or eliminating adverse side effects associated with glucosidase inhibition, the method comprising the administration to the patient of a therapeutically effective amount of a pharmaceutical composition consisting essentially of an imino sugar acid of the formula (G2):

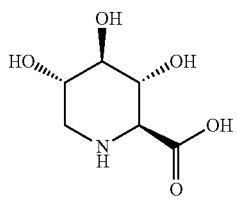

(G2)

or a pharmaceutically acceptable salt thereof; and one or more pharmaceutically acceptable excipients.
2. A method according to claim 1 wherein the adverse side effects associated with glucosidase inhibition that are reduced or eliminated are gastric side effects.
3. A method according to claim 1 wherein the therapeutically effective amount of pharmaceutical composition administered is such that the imino sugar acid contained therein is administered at a dose of 0.1 to 50 mg per kilogram body weight per day.
4. A method according to claim 2 wherein the therapeutically effective amount of pharmaceutical composition administered is such that the imino sugar acid contained therein is administered at a dose of 0.1 to 50 mg per kilogram body weight per day.
5. A method according to claim 3 wherein the isolated imino sugar acid is administered at a dose of 1 to 5 mg per kilogram body weight per day.
6. A method according to claim 4 wherein the isolated imino sugar acid is administered at a dose of 1 to 5 mg per kilogram body weight per day.
7. A method according to claim 1 wherein the pharmaceutical composition is a unit dosage form.
8. A method according to claim 1 wherein the pharmaceutical composition is a tablet.
9. A method according to claim 1 wherein the pharmaceutical composition is a capsule.
10. A method of treating type 2 diabetes in a human patient while reducing or eliminating adverse side effects associated with glucosidase inhibition, the method comprising the administration to the patient of a therapeutically effective amount of a pharmaceutical composition comprising a sole active ingredient consisting of an imino sugar acid of the formula (G2):

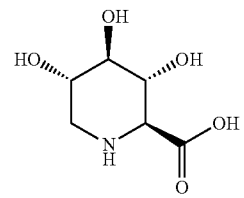

(G2)

or a pharmaceutically acceptable salt thereof; and one or more pharmaceutically acceptable excipients.
11. A method according to claim 10 wherein the adverse side effects associated with glucosidase inhibition that are reduced or eliminated are gastric side effects.
12. A method according to claim 10 wherein the therapeutically effective amount of pharmaceutical composition administered is such that the imino sugar acid contained therein is administered at a dose of 0.1 to 50 mg per kilogram body weight per day.
13. A method according to claim 10 wherein the therapeutically effective amount of pharmaceutical composition administered is such that the isolated imino sugar acid is administered at a dose of 1 to 5 mg per kilogram body weight per day.
14. A method according to claim 10 wherein the pharmaceutical composition is a unit dosage form.
15. A method according to claim 10 wherein the pharmaceutical composition is a tablet.
16. A method according to claim 10 wherein the pharmaceutical composition is a capsule.
17. A method of treating type 2 diabetes in a human patient while reducing or eliminating adverse side effects associated with glucosidase inhibition, the method comprising the administration to the patient of a pharmaceutical composition comprising a therapeutically effective amount of an active agent and one or more pharmaceutically acceptable excipients, wherein the active agent consists of an imino sugar acid of the formula (G2):

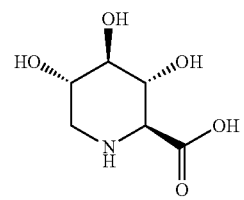

(G2)

or a pharmaceutically acceptable salt thereof.

18. A method according to claim 17 wherein the therapeutically effective amount of pharmaceutical composition administered is such that the imino sugar acid contained therein is administered at a dose of 0.1 to 50 mg per kilogram body weight per day.

19. A method according to claim 17 wherein the therapeutically effective amount of pharmaceutical composition administered is such that the isolated imino sugar acid is administered at a dose of 1 to 5 mg per kilogram body weight per day.

20. A method according to claim 17 wherein the pharmaceutical composition is a tablet or a capsule.

\* \* \* \* \*